United States Patent
Lim et al.

(10) Patent No.: US 10,439,153 B2
(45) Date of Patent: Oct. 8, 2019

(54) COMPOUND AND ORGANIC SOLAR CELL COMPRISING SAME

(71) Applicant: LG CHEM, LTD., Seoul (KR)

(72) Inventors: Bogyu Lim, Daejeon (KR); Jaechol Lee, Daejeon (KR); Jiyoung Lee, Daejeon (KR); Younshin Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 14 days.

(21) Appl. No.: 15/559,377

(22) PCT Filed: Apr. 28, 2016

(86) PCT No.: PCT/KR2016/004447
§ 371 (c)(1),
(2) Date: Sep. 18, 2017

(87) PCT Pub. No.: WO2016/175573
PCT Pub. Date: Nov. 3, 2016

(65) Prior Publication Data
US 2018/0069184 A1    Mar. 8, 2018

(30) Foreign Application Priority Data

Apr. 28, 2015  (KR) .................. 10-2015-0059860
Apr. 22, 2016  (KR) .................. 10-2016-0049483

(51) Int. Cl.
*H01L 31/00* (2006.01)
*H01L 51/00* (2006.01)
(Continued)

(52) U.S. Cl.
CPC ............ *H01L 51/0094* (2013.01); *C07F 7/02* (2013.01); *C07F 7/1804* (2013.01); *H01L 31/0224* (2013.01); *H01L 51/0068* (2013.01); *H01L 51/0069* (2013.01); *H01L 51/0071* (2013.01); *H01L 51/0074* (2013.01);
(Continued)

(58) Field of Classification Search
CPC ............ H01L 51/0094; H01L 31/0224; H01L 51/0068; H01L 51/0069; H01L 51/0074; H01L 51/0071; H01L 51/4253; H01L 51/0047; C07F 7/1804; C07F 7/02; Y02E 10/549; G01R 33/46; G01N 2021/3155; C07D 409/10
See application file for complete search history.

(56) References Cited

U.S. PATENT DOCUMENTS 5,331,183 A    7/1994  Sariciftci et al.
5,454,880 A    10/1995 Sariciftci et al.

FOREIGN PATENT DOCUMENTS

JP   2015-65266 A    4/2015
KR   10-1139055 B1   4/2012
WO   2014/128277 A1  8/2014

OTHER PUBLICATIONS

Song et al, "Highly Conductive Poly(phenylene thienylene)s: m-Phenylene Linkages Are Not Always Bad," Macromolecules, 2005, 38 (11), pp. 4569-4576 (Year: 2005).*

(Continued)

*Primary Examiner* — Angelo Trivisonno
(74) *Attorney, Agent, or Firm* — Meyer Bigel, P.A.

(57) ABSTRACT

The present specification relates to a compound and an organic solar cell comprising the same.

15 Claims, 17 Drawing Sheets

(51) Int. Cl.
  *C07F 7/02* (2006.01)
  *H01L 31/0224* (2006.01)
  *C07F 7/18* (2006.01)
  C07D 409/10 (2006.01)
  G01N 21/31 (2006.01)
  G01R 33/46 (2006.01)
  H01L 51/42 (2006.01)

(52) U.S. Cl.
  CPC ... *C07D 409/10* (2013.01); *G01N 2021/3155* (2013.01); *G01R 33/46* (2013.01); *H01L 51/0047* (2013.01); *H01L 51/4253* (2013.01); *Y02E 10/549* (2013.01)

(56) References Cited

OTHER PUBLICATIONS

Erjing Wang et al., "Syntheses and properties of cyano and dicyanovinyl-substituted oligomers as organic semiconductors", Synthetic Metals, 2009, vol. 159, No. 13, pp. 1298-1301.
Changsik Song et al., "Highly Conductive Poly(phenylene thienylene)s: m-Phenylene Linkages Are Not Always Bad", Macromolecules, 2005, vol. 38, No. 11, pp. 4569-4576.
Mei et al, Siloxane-Terminated Solubilizing Side Chains: Bringing Conjugated Polymer Backbones Closer and Boosting Hole Mobilities in Thin-Film Transistors, Journal of the American Chemical Society, 2011, vol. 133, No. 50, pp. 20130-20133.
Lei et al, Influence of Alkyl Chain Branching Positions on the Hole Mobilities of Polymer Thin-Film Transistors, Advanced Materials, 2012, vol. 24, pp. 6457-6461.

\* cited by examiner

COMPOUND AND ORGANIC SOLAR CELL COMPRISING SAME

TECHNICAL FIELD

This application is a National Stage Application of International Application No. PCT/KR2016/004447 filed on Apr. 28, 2016, which claims the benefit of Korean Patent Application No. 10-2015-0059860 filed on Apr. 28, 2015 and Korean Patent Application No. 10-2016-0049483 filed on Apr. 22, 2016, all of which are hereby incorporated by reference in their entirety for all purposes as if fully set forth herein.

The present specification relates to a compound and an organic solar cell comprising the same.

BACKGROUND ART

An organic solar cell is a device capable of directly converting solar energy to electric energy by applying a photovoltaic effect. Solar cells are divided into inorganic solar cells and organic solar cells depending on the materials forming a thin film. Typical solar cells are fabricated using a p-n junction by doping crystalline silicon (Si), an inorganic semiconductor. Electrons and holes generated by light absorption spread to p-n junction points, are accelerated by the electric field, and migrate to an electrode. Power conversion efficiency of this process is defined as a ratio of power given to an external circuit and solar power put into a solar cell, and the ratio has been accomplished up to 24% when measured under a currently standardized hypothetical solar irradiation condition. However, existing inorganic solar cells already has a limit in economic feasibility and material supplies, and therefore, organic material semiconductor solar cells that are readily processed, inexpensive and have various functions have been highly favored as a long-term alternative energy source.

For solar cells, it is important to increase efficiency so as to output as much electric energy as possible from solar energy. In order to improve efficiency of such solar cells, generating as much excitons as possible inside a semiconductor is important, however, taking the generated charges outside without loss is also important. One of the reasons for the charge loss is the dissipation of the generated electrons and holes by recombination. Various methods for delivering the generated electrons or holes to an electrode without loss have been proposed, however, most of the methods require additional processes, and accordingly, the fabricating costs may increase.

DISCLOSURE

Technical Problem

The present specification is directed to providing a compound and an organic solar cell comprising the same.

Technical Solution

One embodiment of the present specification provides a compound represented by the following Chemical Formula 1.

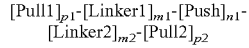   [Chemical Formula 1]

In Chemical Formula 1,
n1 is an integer of 1 to 3,
m1, m2, p1 and p2 are each an integer of 0 to 3,
when n1, m1, m2, p1 and p2 are 2 or greater, structures in the two or more square brackets are the same as or different from each other,
when p1 is 0, hydrogen or hydrocarbon bonds to Linker1 at the end instead of Pull1,
when p2 is 0, hydrogen or hydrocarbon bonds to Linker2 at the end instead of Pull2,
Push is any one of the following structures,

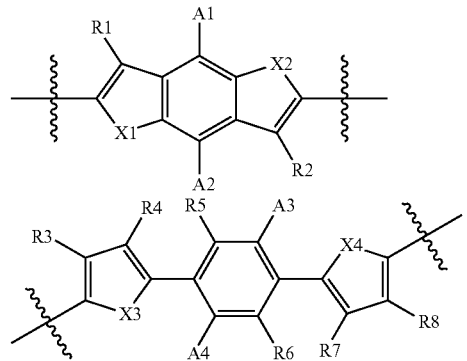

in the structures,
X1 to X4 are the same as or different from each other, and each independently CRR', NR, O, SiRR', PR, S, GeRR', Se or Te,
R, R', R1 to R8, A3 and A4 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, or R5 and R6; or A3 and A4 are represented by the following Chemical Formula 2,
A1 and A2 are the same as or different from each other, and each independently represented by the following Chemical Formula 2,

[Chemical Formula 2]

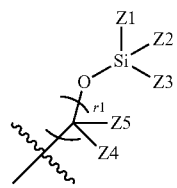

in Chemical Formula 2,
r1 is an integer of 0 to 3,
when r1 is 2 or greater, structures in the two or more parentheses are the same as or different from each other,
Z1 to Z5 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group,

is a site bonding to Chemical Formula 1,

Linker1 and Linker2 are the same as or different from each other, and a divalent linker, and Pull1 and Pull2 are the same as or different from each other, and an electron accepting structure.

Another embodiment of the present specification provides an organic solar cell comprising a first electrode; a second electrode provided opposite to the first electrode; and one or more organic material layers provided between the first electrode and the second electrode and comprising a photoactive layer, wherein one or more layers of the organic material layers comprise the above-described compound.

Advantageous Effects

A compound according to one embodiment of the present specification comprises a Push structure having an electron donating property and a Pull structure having an electron accepting property. In addition, the compound comprises a linker linking Push and Pull and having excellent planarity, is capable of maximizing exciton polarization since the formed excitons can quickly migrate within the molecule, and is capable of have a low band gap property.

In addition, the compound according to one embodiment of the present specification comprises a structure of Chemical Formula 2, a bulky side chain, in Push of Chemical Formula 1 enhancing solubility and viscosity, and can suppress aggregation by reducing interaction between the compounds. As a result, when using Chemical Formula 1 comprising Chemical Formula 2 as a donor to form a bulk-heterojunction film with an acceptor material, the compound is capable of suppressing a donor size increase.

Furthermore, the compound according to one embodiment of the present specification comprises a structure of Chemical Formula 2 in Push, and can provide elasticity to the compound.

Accordingly, the compound can be used as an organic material layer material of an organic solar cell, and an organic solar cell comprising the same is capable of exhibiting excellent properties in increasing open circuit voltage and short circuit current, increasing efficiency and/or the like.

The compound according to one embodiment of the present specification can be used either alone or as a mixture with other materials in an organic solar cell, and enhancement in the efficiency, enhancement in the device lifespan caused by properties of the compound such as thermal stability, and the like, can be expected.

Figure 1:
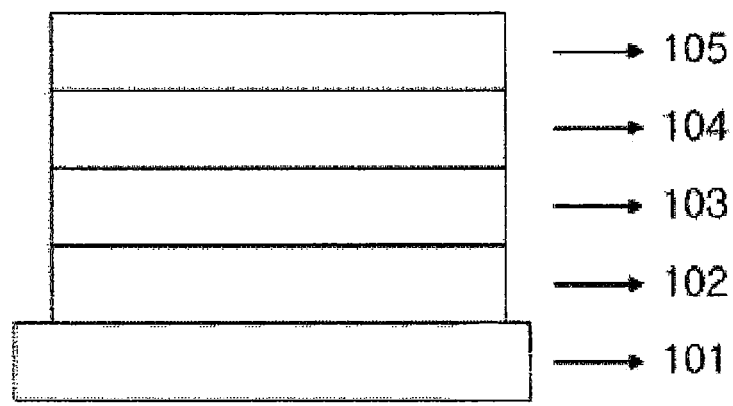
FIG. 1 is a diagram illustrating an organic solar cell according to one embodiment of the present specification.

101: Substrate
102: First Electrode
103: Hole Transfer Layer
104: Photoactive Layer
105: Second Electrode

MODE FOR DISCLOSURE

Hereinafter, the present specification will be described in detail.

One embodiment of the present specification provides a compound represented by Chemical Formula 1.

In the present specification, a description of a certain part "comprising" certain constituents means capable of further comprising other constituents, and does not exclude other constituents unless particularly stated on the contrary.

In the present specification, a description of one member being placed "on" another member comprises not only a case of the one member adjoining the another member but a case of still another member being present between the two members.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an amine group; an arylphosphine group; a phosphine oxide group; an aryl group; and a heterocyclic group, or being substituted with a substituent linking two or more substituents among the substituents illustrated above, or having no substituents. For example, "a substituent linking two or more substituents" may comprise a biphenyl group. In other words, a biphenyl group may be an aryl group, or interpreted as a substituent linking two phenyl groups.

In the present specification,

means a site bonding to other substituents or bonding sites.

In the present specification, the halogen group may comprise fluorine, chlorine, bromine or iodine.

In the present specification, the number of carbon atoms of the imide group is not particularly limited, but is preferably from 1 to 30. Specifically, compounds having structures as below may be comprised, however, the imide group is not limited thereto.

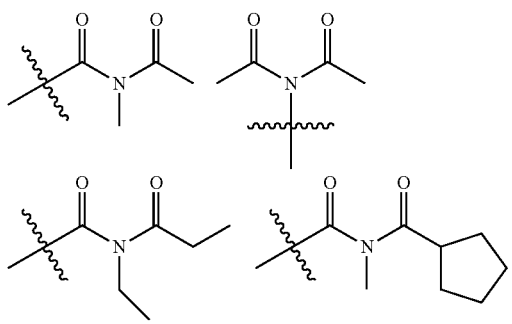

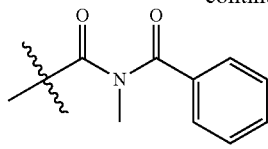

In the present specification, in the amide group, the nitrogen of the amide group may be substituted with hydrogen, a linear, branched or cyclic alkyl group having 1 to 30 carbon atoms or an aryl group having 6 to 30 carbon atoms. Specifically, compounds having the following structural formulae may be comprised, however, the amide group is not limited thereto.

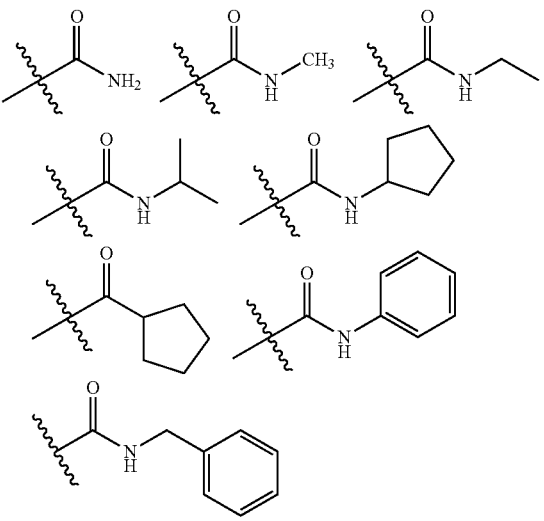

In the present specification, the number of carbon atoms of the carbonyl group is not particularly limited, but is preferably from 1 to 30. Specifically, compounds having structures as below may be comprised, however, the carbonyl group is not limited thereto.

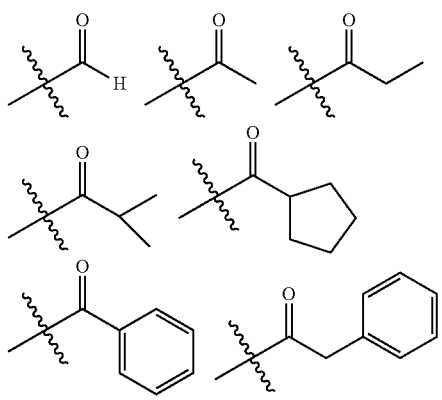

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be comprised, however, the ester group is not limited thereto.

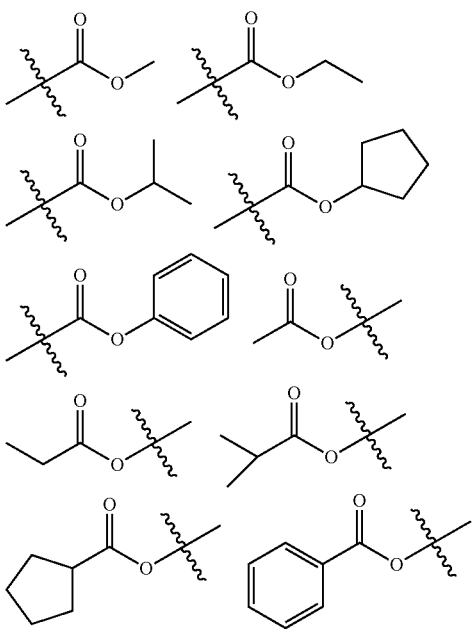

In the present specification, the alkyl group may be linear or branched, and the number of carbon atoms is not particularly limited, but is preferably from 1 to 30. Specific examples thereof may comprise methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenxyloxy and the like, but are not limited thereto.

In the present specification, the amine group may be selected from the group consisting of —$NH_2$; an alkylamine group; an N-arylalkylamine group; an arylamine group; an N-arylheteroarylamine group; an N-alkylheteroarylamine group and a heteroarylamine group, and the number of carbon atoms is, although not particularly limited thereto, preferably from 1 to 30. Specific examples of the amine group may comprise a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specific examples of the alkylthioxy group may comprise a methylthioxy group, an ethylthioxy group, a tert-butylthioxy group, a hexylthioxy group, an octylthioxy group and the like, and specific examples of the alkylsulfoxy group may comprise mesyl, an ethylsulfoxy group, a propylsulfoxy group, a butylsulfoxy group and the like, however, the examples are not limited thereto.

In the present specification, the alkenyl group may be linear or branched, and although not particularly limited thereto, the number of carbon atoms is preferably from 2 to 30. Specific examples thereof may comprise vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —$BR_{100}R_{101}$, and $R_{100}$ and $R_{101}$ are the same as or different from each other and may be each independently selected from the group consisting of hydrogen; deuterium; halogen; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may comprise a diphenylphosphine oxide group, a dinaphthylphosphine oxide group and the like, but are not limited thereto.

In the present specification, the aryl group may be monocyclic or multicyclic.

When the aryl group is a monocyclic aryl group, the number of carbon atoms is not particularly limited, but is preferably from 6 to 30. Specific examples of the monocyclic aryl group may comprise a phenyl group, a biphenyl group, a terphenyl group and the like, but are not limited thereto.

When the aryl group is a multicyclic aryl group, the number of carbon atoms is not particularly limited, but is preferably from 10 to 30. Specific examples of the multicyclic aryl group may comprise a naphthyl group, an anthracenyl group, a phenanthryl group, a triphenyl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

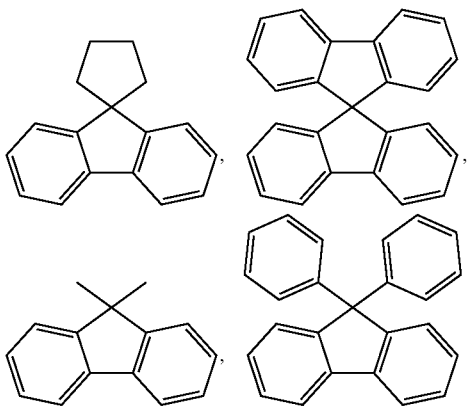

and the like may be comprised. However, the structure is not limited thereto.

In the present specification, the aryl group in the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group may comprise a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and specific examples of the arylthioxy group may comprise a phenylthioxy group, a 2-methylphenylthioxy group, a 4-tert-butylphenylthioxy group and the like, and specific examples of the arylsulfoxy group may comprise a benzenesulfoxy group, a p-toluenesulfoxy group and the like, however, the examples are not limited thereto.

In the present specification, examples of the arylamine group comprise a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group comprising two or more aryl groups may comprise monocyclic aryl groups, multicyclic aryl groups, or both monocyclic aryl groups and multicyclic aryl groups. For example, the aryl group in the arylamine group may be selected from among the examples of the aryl group described above.

In the present specification, the heteroaryl group is a group comprising one or more atoms that are not carbon, that is, heteroatoms, and specifically, the heteroatom may comprise one or more atoms selected from the group consisting of O, N, Se, S and the like. The number of carbon atoms is not particularly limited, but is preferably from 2 to 30, and the heteroaryl group may be monocyclic or multicyclic. Examples of the heterocyclic group may comprise a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a triazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, examples of the heteroarylamine group comprise a substituted or unsubstituted monoheteroarylamine group, a substituted or unsubstituted diheteroarylamine group, or a substituted or unsubstituted triheteroarylamine group. The heteroarylamine group comprising two or more heteroaryl groups may comprise monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, examples of the heteroaryl group in the N-arylheteroarylamine group and the N-alkylheteroarylamine group are the same as the examples of heteroaryl group described above.

In the present specification, the heterocyclic group may be monocyclic or multicyclic, may be aromatic, aliphatic or a fused ring of aromatic and aliphatic, and may be selected from among the examples of the heteroaryl group.

According to one embodiment of the present specification, in Chemical Formula 1, Push has an oxidation property in the heterocyclic compound.

According to one embodiment of the present specification, in Chemical Formula 1, Pull1 and Pull2 have a reduction property in the heterocyclic compound.

According to one embodiment of the present specification, when measuring Push, Pull1 and Pull2 using cyclic voltammetry (CV), Push relatively has an oxidation property compared to Pull1 and Pull2, and Pull1 and Pull2 relatively have a reduction property compared to Push.

However, in the present specification, the oxidation property and the reduction property are relative, and Push may have, although having an oxidation property, a reduction property as well, and Pull1 and Pull2 may have, although having a reduction property, an oxidation property as well.

In the compound according to one embodiment of the present specification, Push relatively functions as an electron donor, and Pull1 and Pull2 function as an electron acceptor.

In this case, electrons in a lowest unoccupied molecular orbital (LUMO) state are localized relatively in Pull1 and Pull2. Accordingly, polarization is present between Push, and Pull1 and Pull2.

In the present specification, electron localization may be maximized by introducing Linker1 and Linker2 having relatively excellent planarity and having a conjugation structure between Push, and Pull1 and Pull2, and moving the electrons toward Pull1 and Pull2 in the compound. In this case, formed excitons may quickly migrate within the molecule, and exciton polarization may be maximized, and as a result, a low band gap property may be obtained.

In the present specification, an energy level means magnitude of energy. Accordingly, even when an energy level is expressed in a negative (−) direction from a vacuum level, the energy level is interpreted to mean an absolute value of the corresponding energy value. For example, a HOMO energy level means a distance from a vacuum level to a highest occupied molecular orbital. In addition, a LUMO energy level means a distance from a vacuum level to a lowest unoccupied molecular orbital.

In addition, the compound according to one embodiment of the present specification comprises a structure represented by the following Chemical Formula 2, a bulky side chain, in Push, and therefore, solubility and viscosity may be enhanced.

In addition, the compound according to one embodiment of the present specification comprises a structure of the following Chemical Formula 2, a bulky side chain, in Push of Chemical Formula 1, and therefore, may suppress aggregation by reducing interaction between a backbone and a backbone of electron donor materials in a device. As a result, when a bulk-heterojunction film is formed using Chemical Formula 1 comprising the following Chemical Formula 2 as a donor with an acceptor material, the compound may suppress a donor size increase.

In addition, the compound according to one embodiment of the present specification comprises a structure of the following Chemical Formula 2 in Push, and therefore, may provide elasticity to the compound. In this case, the compound may be used as a material of a flexible device.

Accordingly, high current and high efficiency may be expected in a device comprising an organic solar cell that comprises the compound according to one embodiment of the present specification.

According to one embodiment of the present specification, Push comprises one, two or more selected from the group consisting of a substituted or unsubstituted arylene group; and a substituted or unsubstituted divalent heterocyclic group comprising one or more of N, O, S, Si and Ge.

According to one embodiment of the present specification, Push comprises one, two or more selected from the group consisting of a substituted or unsubstituted arylene group having 6 to 30 carbon atoms; and a substituted or unsubstituted divalent heterocyclic group having 2 to 30 carbons and comprising one or more of N, O, S, Si and Ge.

According to one embodiment of the present specification, Push is any one of the following structures.

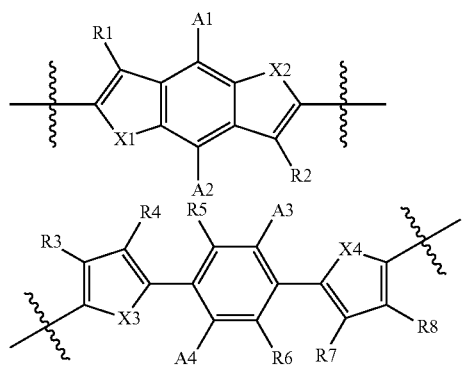

In the structures,

X1 to X4 are the same as or different from each other, and each independently CRR', NR, O, SiRR', PR, S, GeRR', Se or Te, R, R', R1 to R8, A3 and A4 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, or R5 and R6; or A3 and A4 are represented by the following Chemical Formula 2, A1 and A2 are the same as or different from each other, and each independently represented by the following Chemical Formula 2,

[Chemical Formula 2]

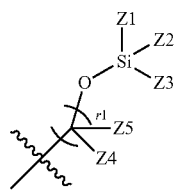

in Chemical Formula 2, r1 is an integer of 0 to 3, when r1 is 2 or greater, structures in the two or more parentheses are the same as or different from each other, Z1 to Z5 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

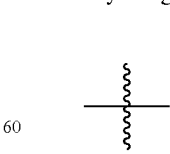

is a site bonding to Chemical Formula 1.

According to one embodiment of the present specification, in Chemical Formula 2, Z1 to Z5 are the same as or different from each other, and each independently a substituted or unsubstituted alkyl group.

According to one embodiment of the present specification, Z1 to Z5 are the same as or different from each other, and each independently a substituted or unsubstituted linear or branched alkyl group having 1 to 30 carbon atoms.

According to one embodiment of the present specification, Z1 to Z5 are the same as or different from each other, and each independently a substituted or unsubstituted linear or branched alkyl group having 1 to 20 carbon atoms.

According to one embodiment of the present specification, Z1 to Z5 are the same as or different from each other, and each independently a substituted or unsubstituted linear or branched alkyl group having 1 to 10 carbon atoms.

According to one embodiment of the present specification, Z1 to Z5 are the same as or different from each other, and each independently a substituted or unsubstituted n-hexyl group.

According to one embodiment of the present specification, Z1 is an n-hexyl group.

According to one embodiment of the present specification, Z2 is an n-hexyl group.

According to one embodiment of the present specification, Z3 is an n-hexyl group.

According to one embodiment of the present specification, in Chemical Formula 1, Linker1 and Linker2 are the same as or different from each other, and each independently comprise one, two or more selected from the group consisting of a substituted or unsubstituted arylene group having 6 to 30 carbon atoms; and a substituted or unsubstituted divalent heterocyclic group having 2 to 30 carbon atoms and comprising one or more of N, O, S, Si and Ge.

According to one embodiment of the present specification, Linker1 and Linker2 are the same as or different from each other, and each independently any one of the following structures.

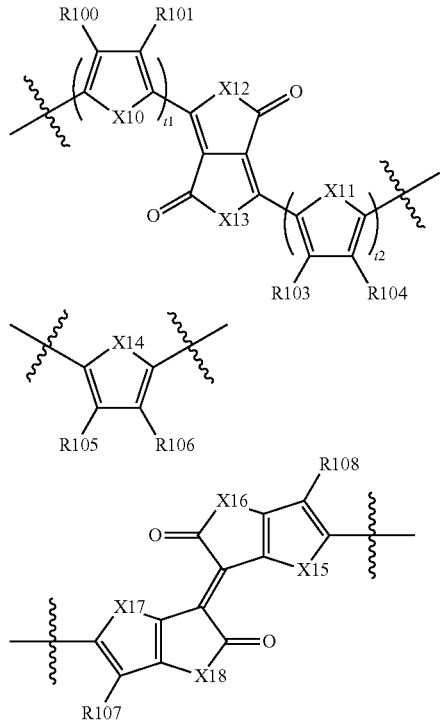

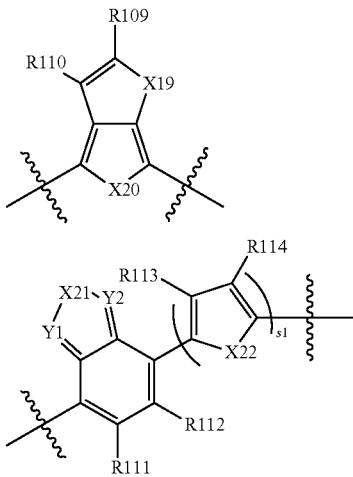

In the structures, t1, t2 and s1 are each an integer of 1 to 3, when t1, t2 and s1 are each 2 or greater, structures in the two or more parentheses are the same as or different from each other, X10 to X22 are the same as or different from each other, and each independently $CR_aR_b$, $NR_a$, O, $SiR_aR_b$, $PR_a$, S, $GeR_aR_b$, Se or Te, Y1 and Y2 are the same as or different from each other, and each independently CR", N, SiR", P or GeR", $R_a$, $R_b$, R" and R100 to R114 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

is a site bonding to Chemical Formula 1.

According to one embodiment of the present specification, in Chemical Formula 1, Pull1 and Pull2 are the same as or different from each other, and each independently a substituted or unsubstituted alkenyl group having 2 to 30 carbon atoms.

Pull1 and Pull2 are the same as or different from each other, and each independently any one of the following structures.

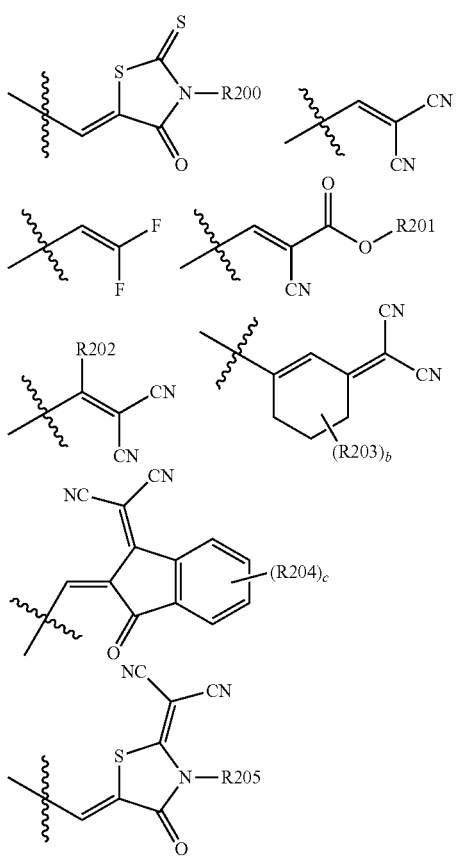

In the structures, b is an integer of 1 to 7, c is an integer of 1 to 4, when b and c are each 2 or greater, structures in the two or more parentheses are the same as or different from each other, R200 to R205 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

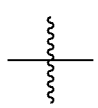

is a site bonding to Chemical Formula 1.

According to one embodiment of the present specification, Chemical Formula 1 may be represented by any one of the following Chemical Formulae 1-1 to 1-3.

[Linker1]$_{m3}$-[Push]$_{n2}$-[Linker2]$_{m4}$      [Chemical Formula 1-1]

[Pull1]$_{p3}$-[Push]$_{n3}$-[Pull2]$_{p4}$      [Chemical Formula 1-2]

[Pull1]$_{p5}$-[Linker1]$_{m5}$-[Push]$_{n4}$-[Linker2]$_{m6}$-[Pull2]$_{p6}$      [Chemical Formula 1-3]

In Chemical Formulae 1-1 to 1-3, n2 to n4, m3 to m6 and p3 to p6 are each an integer of 1 to 3, when n2 to n4, m3 to m6 and p3 to p6 are each 2 or greater, structures in the two or more square brackets are the same as or different from each other, Push, Linker1, Linker2, Pull1 and Pull2 have the same definitions as in Chemical Formula 1, and hydrogen bonds at the end of Linker 1 and Linker 2.

According to one embodiment of the present specification, Chemical Formula 1 may be represented by any one of the following Chemical Formulae 1-4 to 1-6.

[Chemical Formula 1-4]

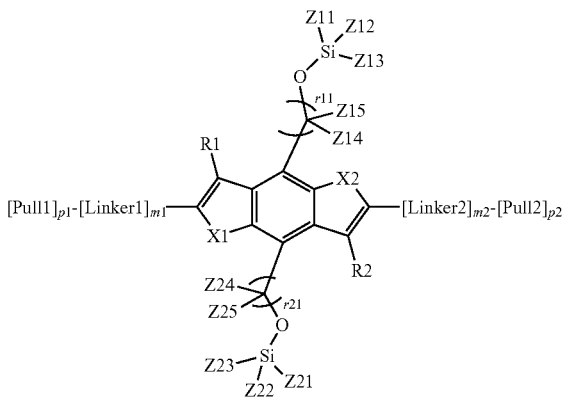

[Chemical Formula 1-5]

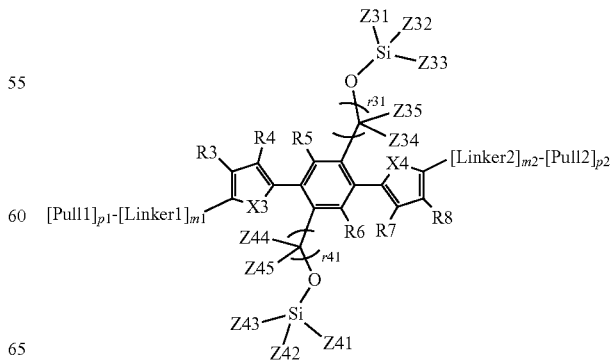

[Chemical Formula 1-6]

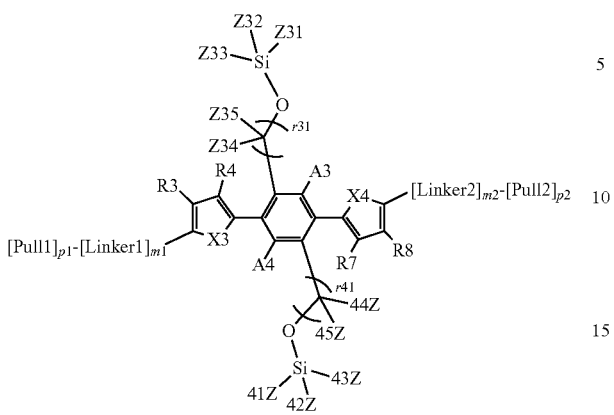

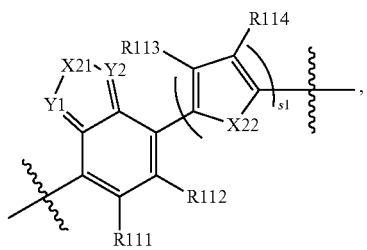

and
in the structure,
s1 is an integer of 1 to 3,
when s1 is 2 or greater, structures in the two or more parentheses are the same as or different from each other,
X21 and X22 are the same as or different from each other, and each independently $CR_aR_b$, $NR_a$, O, $SiR_aR_b$, $PR_a$, S, $GeR_aR_b$, Se or Te,
Y1 and Y2 are the same as or different from each other, and each independently CR", N, SiR", P or GeR",
$R_a$, $R_b$, R" and R111 to R114 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and In Chemical Formulae 1-4 to 1-6, m1, m2, p1, p2, Linker1, Linker2, Pull1 and Pull2 have the same definitions as in Chemical Formula 1, X1 to X4 are the same as or different from each other, and each independently CRR', NR, O, SiRR', PR, S, GeRR', Se or Te, R, R', R1 to R8, A3 and A4 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, r11, r21, r31 and r41 are each an integer of 0 to 3, when r11, r21, r31 and r41 are 2 or greater, structures in the two or more parentheses are the same as or different from each other, and Z11 to Z15, Z21 to Z25, Z31 to Z35 and Z41 to Z45 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group.

According to one embodiment of the present specification, in Chemical Formula 1, Linker1 is

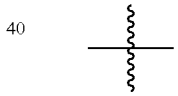

is a site bonding to Chemical Formula 1.

According to one embodiment of the present specification, Linker2 is

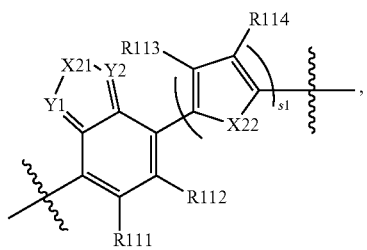

and
in the structure,
s1 is an integer of 1 to 3,
when s1 is 2 or greater, structures in the two or more parentheses are the same as or different from each other,
X21 and X22 are the same as or different from each other, and each independently $CR_aR_b$, $NR_a$, O, $SiR_aR_b$, $PR_a$, S, $GeR_aR_b$, Se or Te, Y1 and Y2 are the same as or different from each other, and each independently CR", N, SiR", P or GeR", $R_a$, $R_b$, R" and R111 to R114 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

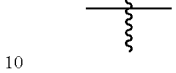

is a site bonding to Chemical Formula 1.

According to one embodiment of the present specification, Chemical Formula 1 is represented by any one of the following Chemical Formulae 1-7 to 1-9.

[Chemical Formula 1-7]

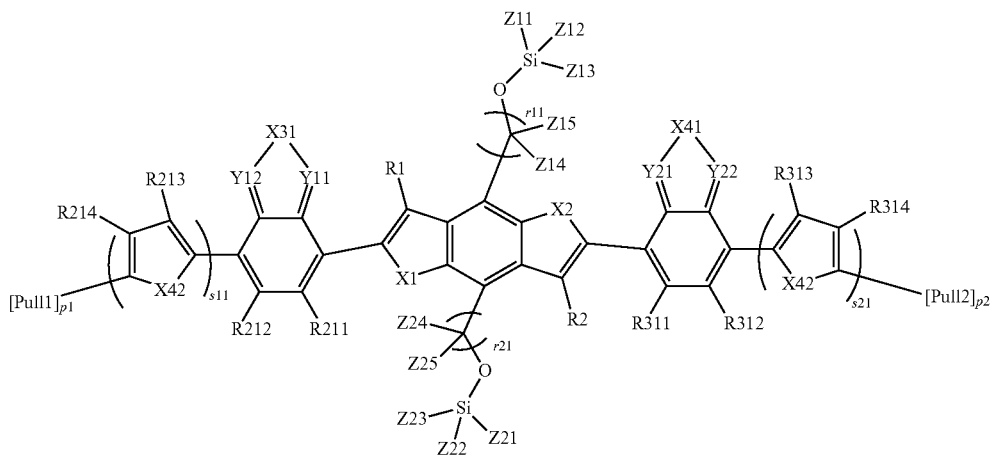

[Chemical Formula 1-8]

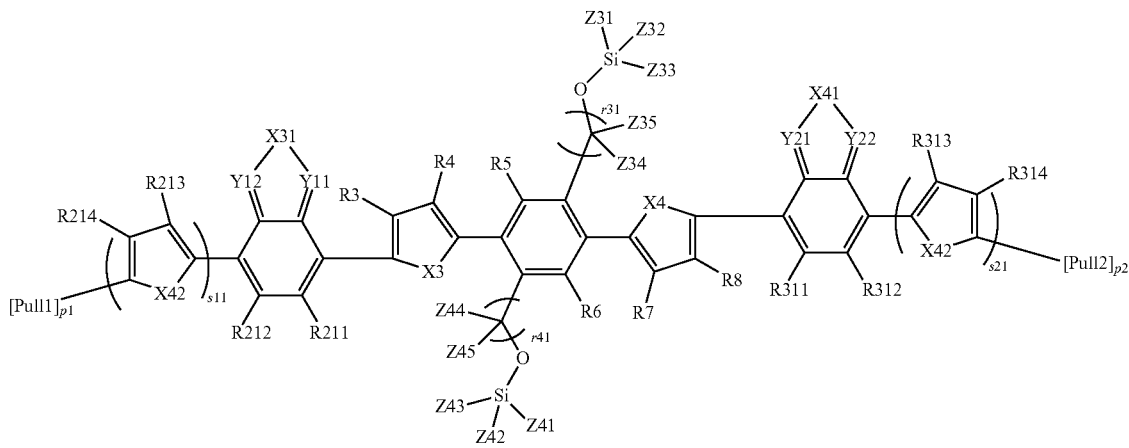

[Chemical Formula 1-9]

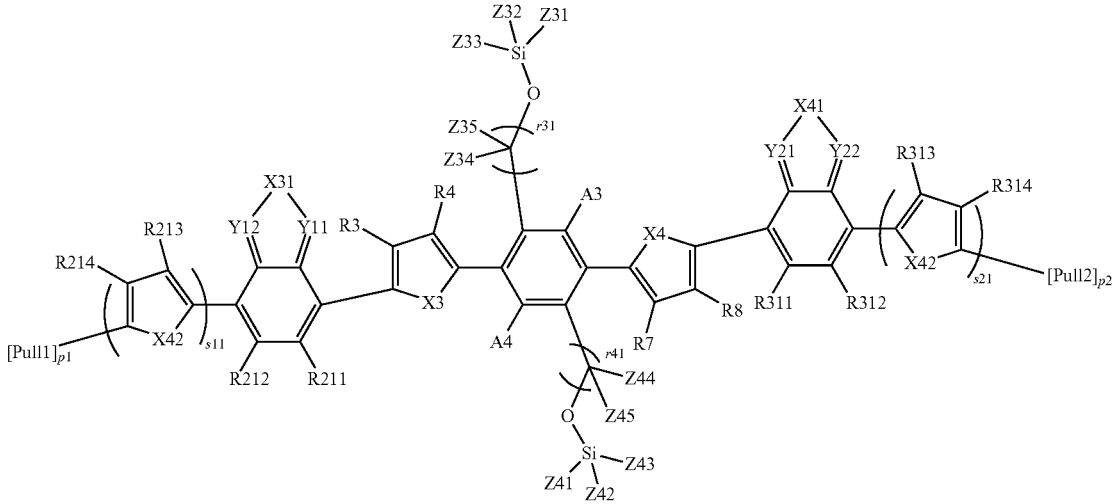

In Chemical Formulae 1-7 to 1-9, p1, p2, Pull1 and Pull2 have the same definitions as in Chemical Formula 1, X1 to X4 are the same as or different from each other, and each independently CRR', NR, O, SiRR', PR, S, GeRR', Se or Te, R, R', R1 to R8, A3 and A4 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, r11, r21, r31 and r41 are each an integer of 0 to 3, when r11, r21, r31 and r41 is 2 or greater, structures in the two or more parentheses are the same as or different from each other, Z11 to Z15, Z21 to Z25, Z31 to Z35 and Z41 to Z45 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, s11 and s21 are each an integer of 1 to 3, when s11 and s21 are each 2 or greater, structures in the two or more parentheses are the same as or different from each other, X31, X32, X41 and X42 are the same as or different from each other, and each independently $CR_aR_b$, $NR_a$, O, $SiR_aR_b$, $PR_a$, S, $GeR_aR_b$, Se or Te, Y11, Y12, Y21 and Y22 are the same as or different from each other, and each independently CR", N, SiR", P or GeR", and $R_a$, $R_b$, R" R211 to R214 and R311 to R314 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group.

According to one embodiment of the present specification, in Chemical Formula 1, Linker1 is in the structure, t1 and t2 are each an integer of 1 to 3, when t1 and t2 are each 2 or greater, structures in the two or more parentheses are the same as or different from each other, X10 to X13 are the same as or different from each other, and each independently $CR_aR_b$, $NR_a$, O, $SiR_aR_b$, $PR_a$, S, $GeR_aR_b$, Se or Te, $R_a$, $R_b$ and R100 to R104 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

is a site bonding to Chemical Formula 1.

According to one embodiment of the present specification, in Chemical Formula 1, Linker2 is

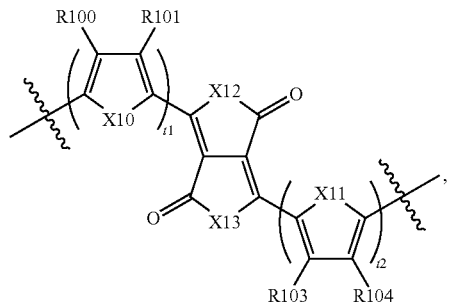

in the structure, t1 and t2 are each an integer of 1 to 3, when t1 and t2 are each 2 or greater, structures in the two or more parentheses are the same as or different from each other, X10 to X13 are the same as or different from each other, and each independently $CR_aR_b$, $NR_a$, O, $SiR_aR_b$, $PR_a$, S, $GeR_aR_b$, Se or Te, $R_a$, $R_b$ and R100 to R104 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, and

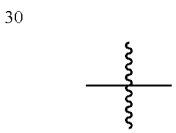

is a site bonding to Chemical Formula 1.

According to one embodiment of the present specification, Chemical Formula 1 is represented by any one of the following Chemical Formulae 1-10 to 1-12.

[Chemical Formula 1-10]

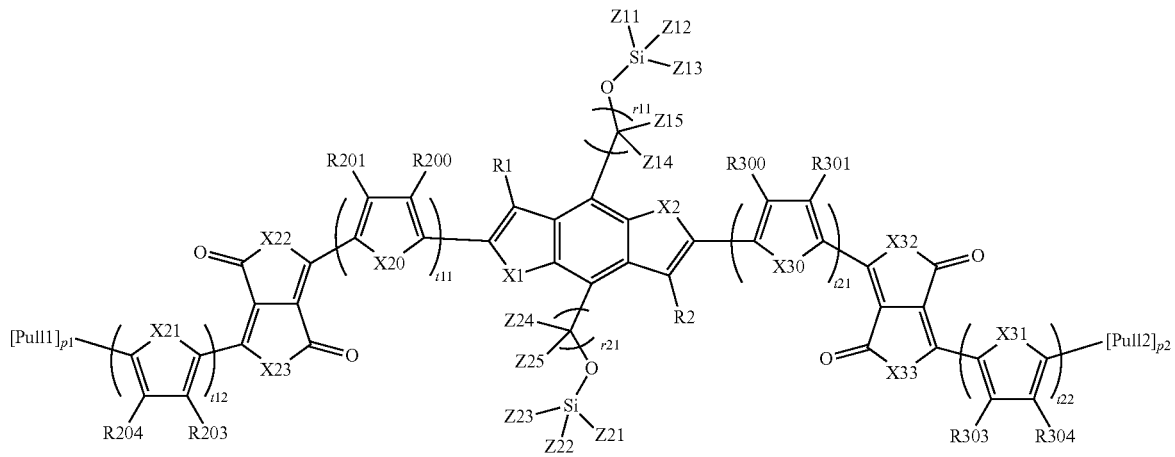

[Chemical Formula 1-11]

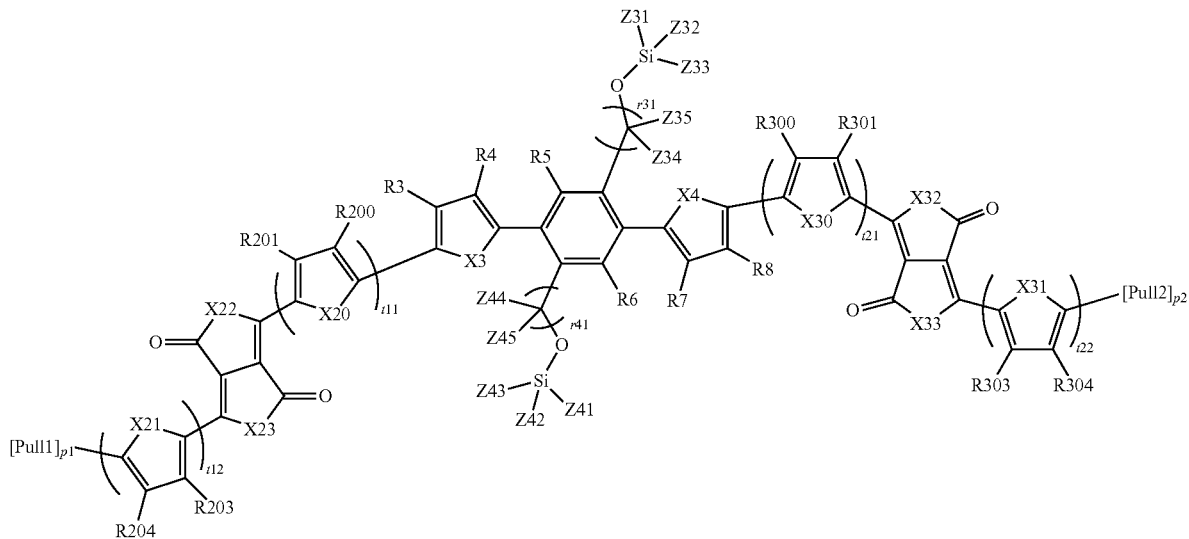

[Chemical Formula 1-12]

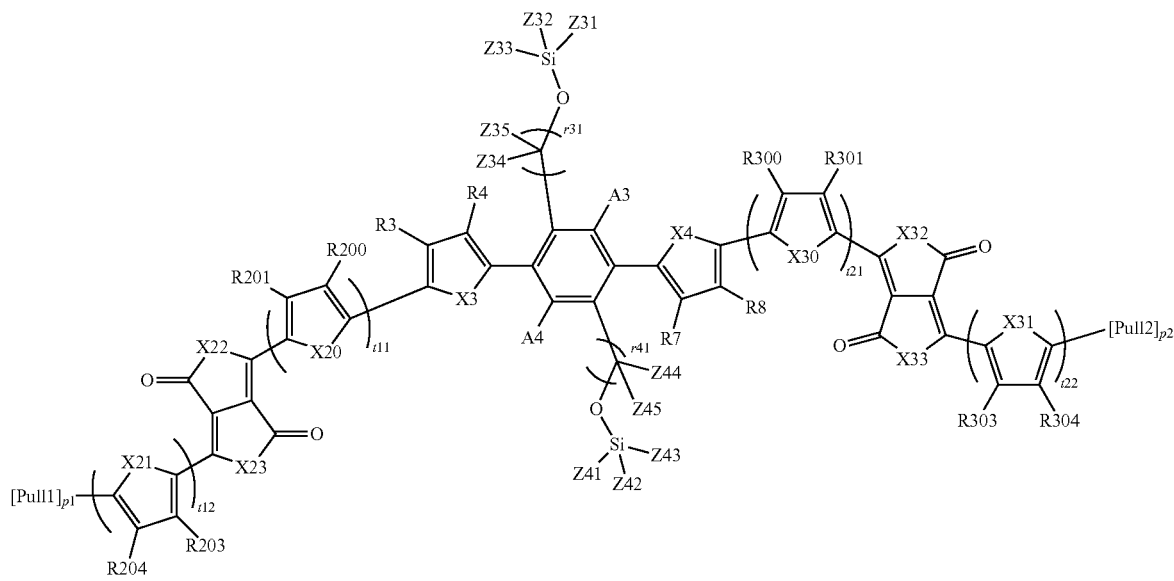

p1, p2, Pull1 and Pull2 have the same definitions as in Chemical Formula 1,

X1 to X4 are the same as or different from each other, and each independently CRR', NR, O, SiRR', PR, S, GeRR', Se or Te, R, R', R1 to R8, A3 and A4 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, r11, r21, r31 and r41 are each an integer of 0 to 3, when r11, r21, r31 and r41 are 2 or greater, structures in the two or more parentheses are the same as or different from each other, Z11 to Z15, Z21 to Z25, Z31 to Z35 and Z41 to Z45 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group, t11, t12, t21 and t22 are each an integer of 1 to 3, when t11, t12, t21 and t22 are each 2 or greater, structures in the two or more parentheses are the same as or different from each other, X20 to X23 and X30 to X33 are the same as or different from each other, and each independently $CR_aR_b$, $NR_a$, O, $SiR_aR_b$, $PR_a$, S, $GeR_aR_b$, Se or Te, and $R_a$, $R_b$, R200 to R204 and R300 to R304 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted aryl group; or a substituted or unsubstituted heterocyclic group.

According to one embodiment of the present specification, in Chemical Formulae 1-4 to 1-6, X1 to X4 are S.

According to one embodiment of the present specification, in Chemical Formula 1-4, R1 and R2 are hydrogen.

According to one embodiment of the present specification, in Chemical Formula 1-5, R3 to R8 are hydrogen.

According to one embodiment of the present specification, in Chemical Formula 1-6, R3, R4, R7, R8, A3 and A4 are hydrogen.

According to one embodiment of the present specification, Chemical Formula 1 may be represented by any one of the following Chemical Formulae 1-13 to 1-15.

[Chemical Formula 1-13]

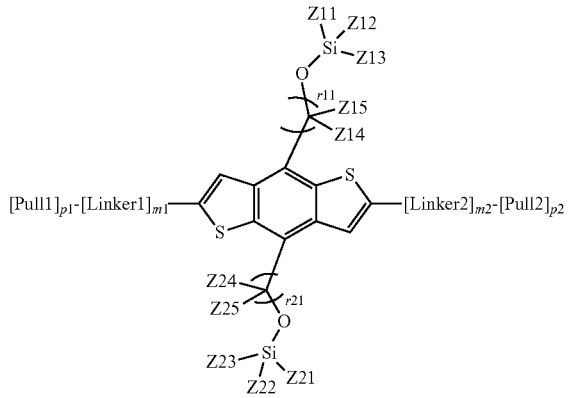

[Chemical Formula 1-14]

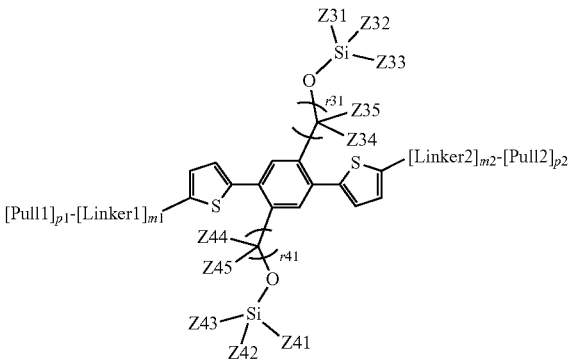

[Chemical Formula 1-15]

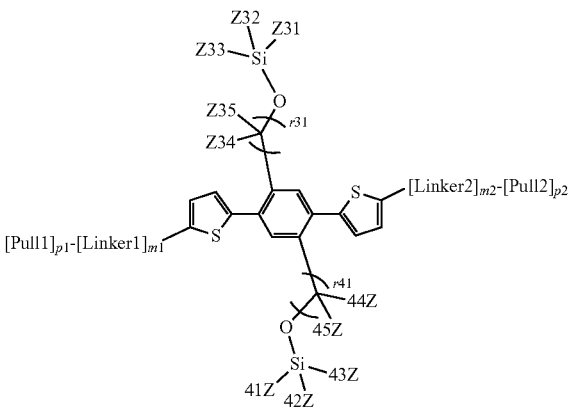

In Chemical Formulae 1-13 to 1-15, m1, m2, p1, p2, Linker1, Linker2, Pull1 and Pull2 have the same definitions as in Chemical Formula 1, r11, r21, r31, r41, Z11 to Z15, Z21 to Z25, Z31 to Z35 and Z41 to Z45 have the same definitions as in Chemical Formulae 1-4 to 1-6.

According to one embodiment of the present specification, Chemical Formula 1 is represented by any one of the following Chemical Formulae 1-16 to 1-18.

[Chemical Formula 1-16]

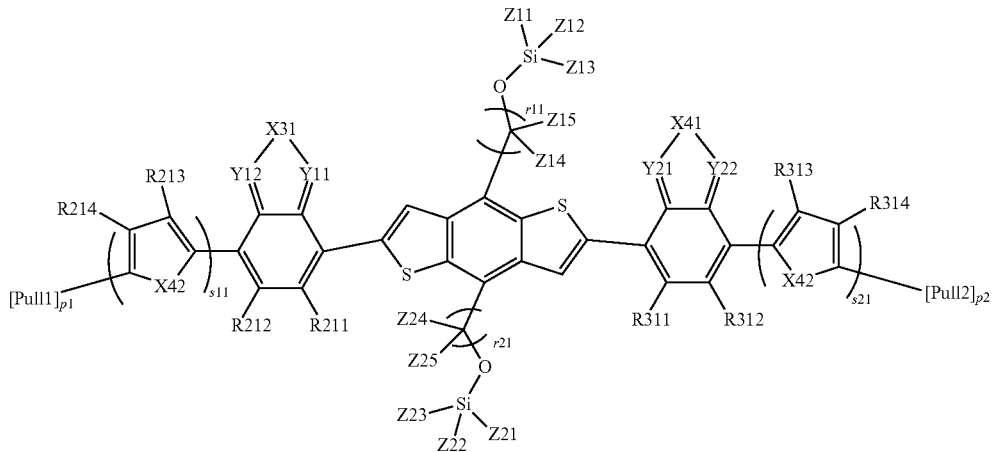

[Chemical Formula 1-17]

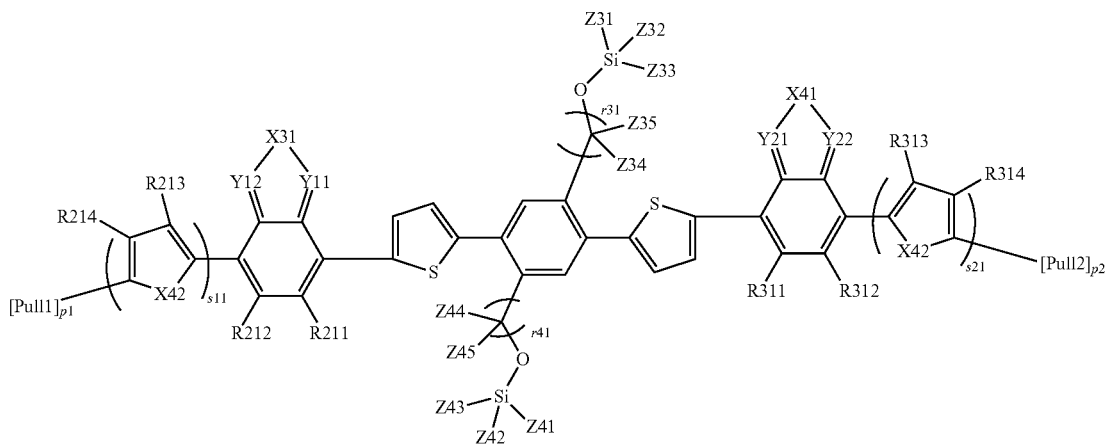

[Chemical Formula 1-18]

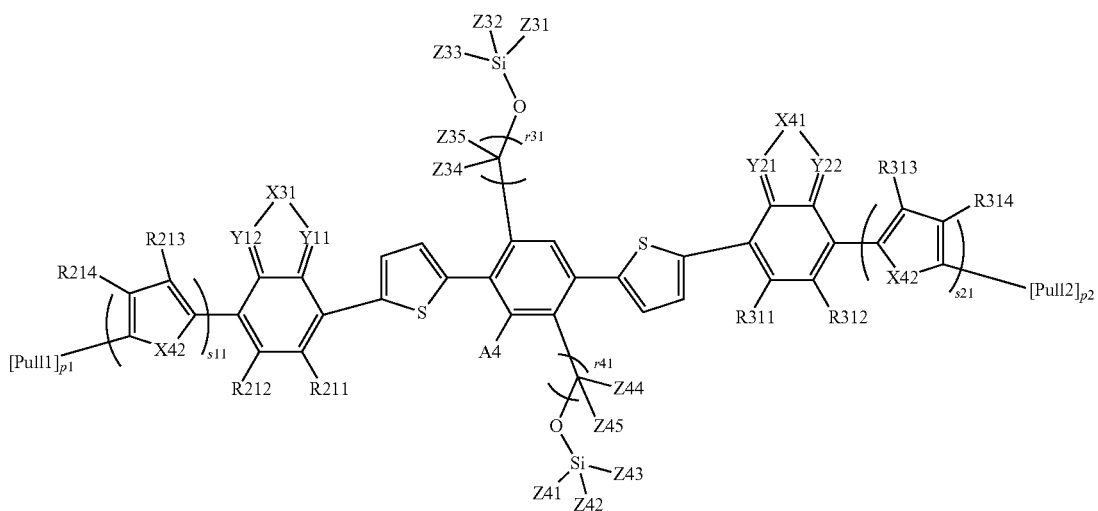

In Chemical Formulae 1-16 to 1-18, p1, p2, Pull1 and Pull2 have the same definitions as in Chemical Formula 1, r11, r21, r31, r41, Z11 to Z15, Z21 to Z25, Z31 to Z35 and Z41 to Z45 have the same definitions as in Chemical Formulae 1-4 to 1-6, and s1, s21, X31, X32, X41, X42, Y11, Y12, Y21, Y22 and R211 to R214 and R311 to R314 have the same definitions as in Chemical Formulae 1-7 to 1-9.

According to one embodiment of the present specification, Chemical Formula 1 is represented by any one of the following Chemical Formulae 1-19 to 1-21.

[Chemical Formula 1-19]
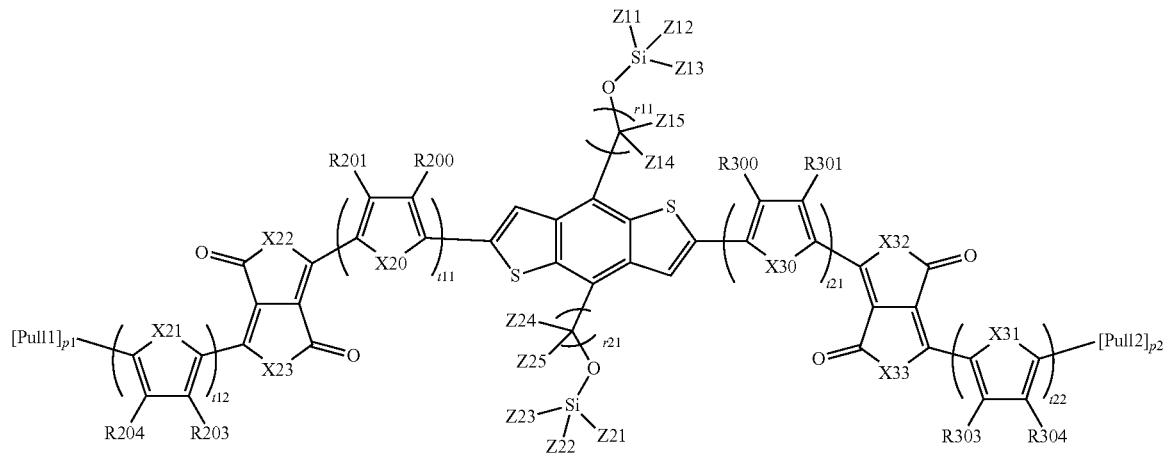
[Chemical Formula 1-20]
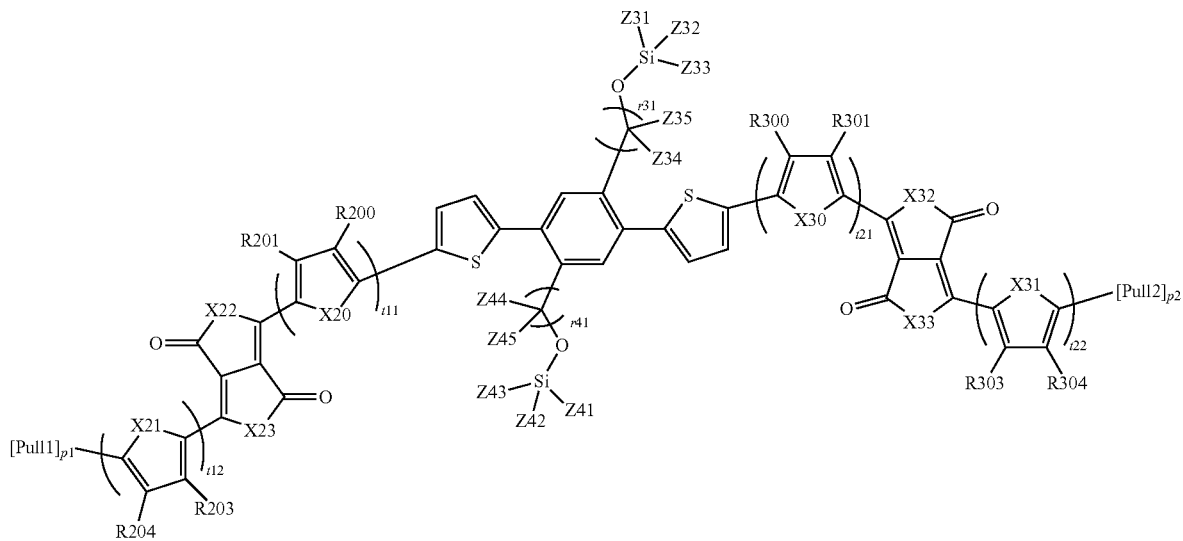
[Chemical Formula 1-21]
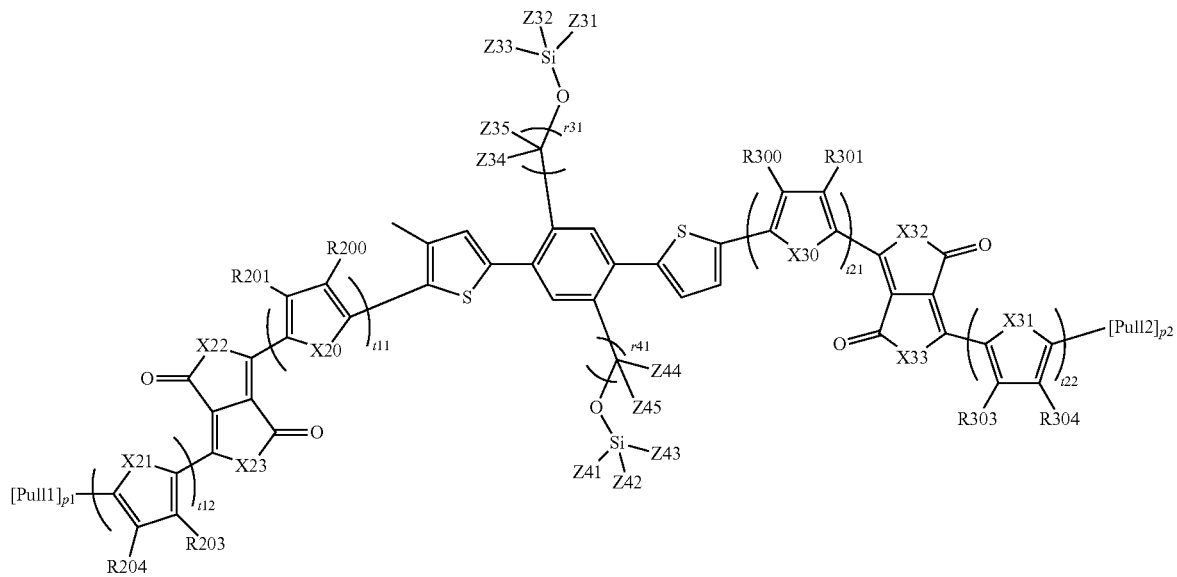

In Chemical Formulae 1-19 to 1-21, p1, p2, Pull1 and Pull2 have the same definitions as in Chemical Formula 1, r11, r21, r31, r41, Z11 to Z15, Z21 to Z25, Z31 to Z35 and Z41 to Z45 have the same definitions as in Chemical Formulae 1-4 to 1-6, and t11, t12, t21, t22, X20 to X23, X30 to X33, R200 to R204 and R300 to R304 have the same definitions as in Chemical Formulae 1-10 to 1-12.

According to one embodiment of the present specification, Z11 to Z13, Z21 to Z23, Z31 to Z33 and Z41 to Z43 are the same as or different from each other, and each independently a substituted or unsubstituted alkyl group.

According to one embodiment of the present specification, Z11 to Z13, Z21 to Z23, Z31 to Z33 and Z41 to Z43 are the same as or different from each other, and each independently a substituted or unsubstituted linear or branched alkyl group having 1 to 30 carbon atoms.

According to one embodiment of the present specification, Z11 to Z13, Z21 to Z23, Z31 to Z33 and Z41 to Z43 are the same as or different from each other, and each independently a substituted or unsubstituted linear or branched alkyl group having 1 to 20 carbon atoms.

According to one embodiment of the present specification, Z11 to Z13, Z21 to Z23, Z31 to Z33 and Z41 to Z43 are the same as or different from each other, and each independently a substituted or unsubstituted linear or branched alkyl group having 1 to 10 carbon atoms.

According to one embodiment of the present specification, Z11 to Z13, Z21 to Z23, Z31 to Z33 and Z41 to Z43 are the same as or different from each other, and each independently a substituted or unsubstituted n-hexyl group.

According to one embodiment of the present specification, Z11 to Z13, Z21 to Z23, Z31 to Z33 and Z41 to Z43 are an n-hexyl group.

According to one embodiment of the present specification, r11, r21, r31 and r41 are 0.

According to one embodiment of the present specification, Chemical Formula 1 is represented by any one of the following Chemical Formulae 1-22 to 1-24.

[Chemical Formula 1-22]

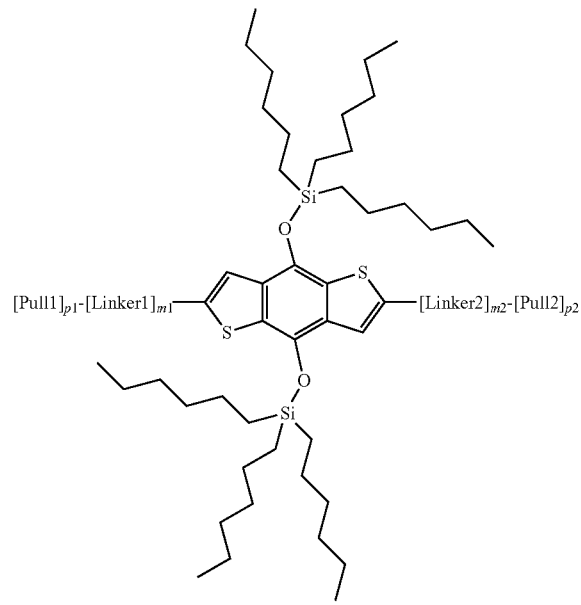

[Chemical Formula 1-23]

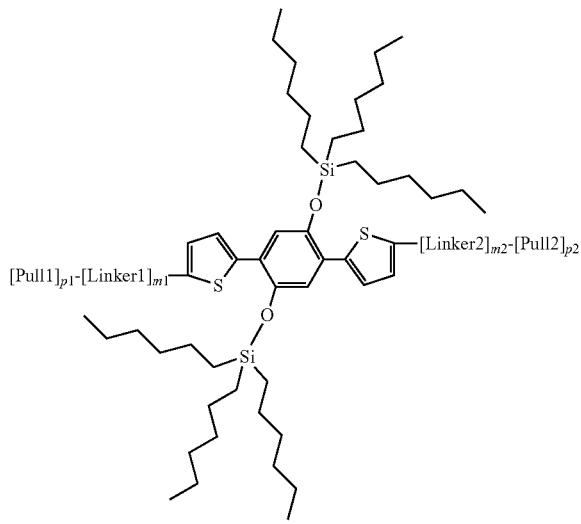

[Chemical Formula 1-24]

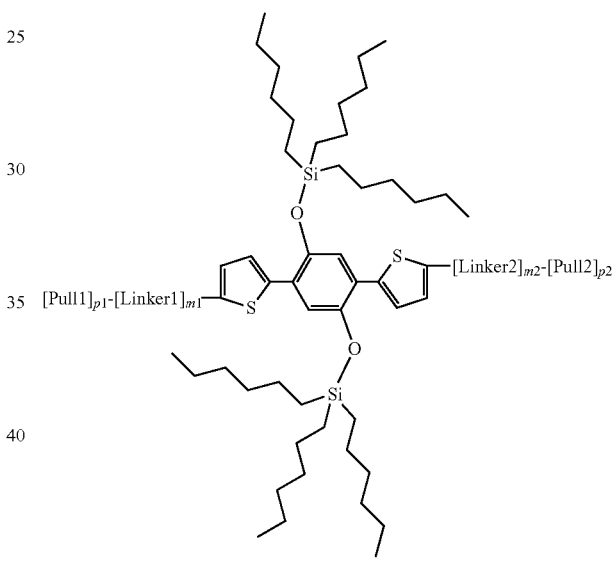

In Chemical Formulae 1-22 to 1-24, m1, m2, p1, p2, Linker1, Linker2, Pull1 and Pull2 have the same definitions as in Chemical Formula 1.

The compound may be prepared based on preparation examples to be described below.

As for the compound according to one embodiment of the present specification, a compound introducing an aldehyde group at each end is prepared by introducing a compound introducing an aldehyde group and a halogen group at the end of Linker1, introducing a compound introducing an aldehyde group and a halogen group at the end of Linker2; and binding with Push. After that, the compound represented by Chemical Formula 1 may be prepared by introducing Pull1 and Pull2 thereto.

The compound according to the present specification may be prepared through a multistep chemical reaction. After preparing monomers through an alkylation reaction, a Grignard reaction, a Suzuki coupling reaction, a Stille coupling reaction and the like, final compounds may be prepared through a carbon-carbon coupling reaction such as a Stille coupling reaction. When a substituent to introduce is a boronic acid or boronic ester compound, a Suzuki coupling reaction may be used for the preparation, and when a substituent to introduce is a tributyltin or trimethyltin compound, a Stille coupling reaction may be used for the preparation, however, the method is not limited thereto.

Another embodiment of the present specification provides an organic solar cell comprising a first electrode; a second electrode provided opposite to the first electrode; and one or more organic material layers provided between the first electrode and the second electrode and comprising a photoactive layer, wherein one or more layers of the organic material layers comprise the compound.

The organic solar cell according to one embodiment of the present specification comprises a first electrode, a photoactive layer and a second electrode. The organic solar cell may further comprise a substrate, a hole transfer layer and/or an electron transfer layer.

In one embodiment of the present specification, when the organic solar cell receives photons from an external light source, electrons and holes are generated between an electron donor and an electron acceptor. The generated holes are transferred to an anode through an electron donor layer.

In one embodiment of the present specification, the organic material layer comprises a hole transfer layer, a hole injection layer or a layer carrying out hole transfer and hole injection at the same time, and the hole transfer layer, the hole injection layer or the layer carrying out hole transfer and hole injection at the same time comprises the compound.

In another embodiment, the organic material layer comprises an electron injection layer, an electron transfer layer or a layer carrying out electron injection and electron transfer at the same time, and the electron injection layer, the electron transfer layer or the layer carrying out electron injection and electron transfer at the same time comprises the compound.

FIG. 1 is a diagram illustrating the organic solar cell according one embodiment of the present specification.

In one embodiment of the present specification, when the organic solar cell receives photons from an external light source, electrons and holes are generated between an electron donor and an electron acceptor. The generated holes are transferred to an anode through an electron donor layer.

In one embodiment of the present specification, the organic solar cell may further comprise additional organic material layers. The organic solar cell may reduce the number of organic material layers by using organic materials having various functions at the same time.

In one embodiment of the present specification, the first electrode is an anode and the second electrode is a cathode. In another embodiment, the first electrode is a cathode and the second electrode is an anode.

In one embodiment of the present specification, in the organic solar cell, the layers may be disposed in the order of a cathode, a photoactive layer and an anode may be disposed in this order, or may be disposed in the order of an anode, a photoactive layer and a cathode, however, the disposition is not limited thereto.

In another embodiment, in the organic solar cell, the layers may be disposed in the order of an anode, a hole transfer layer, a photoactive layer, an electron transfer layer and a cathode, or may be disposed in the order of a cathode, an electron transfer layer, a photoactive layer, a hole transfer layer and an anode, however, the disposition is not limited thereto.

In one embodiment of the present specification, the organic solar cell has a normal structure. In the normal structure, the layers may be laminated in the order of a substrate, an anode, an organic material layer comprising a photoactive layer, and a cathode.

In one embodiment of the present specification, the organic solar cell may have an inverted structure. In the inverted structure, the layers may be laminated in the order of a substrate, a cathode, an organic material layer a photoactive layer, and an anode.

In one embodiment of the present specification, the organic solar cell has a tandem structure.

In the organic solar cell according to one embodiment of the present specification, the photoactive layer may be comprised in one, or two or more layers. In the tandem structure, the photoactive layer may be comprised in two or more layers.

In another embodiment, a buffer layer may be provided between a photoactive layer and a hole transfer layer or between a photoactive layer and an electron transfer layer. Herein, a hole injection layer may be further provided between an anode and the hole transfer layer. In addition, an electron injection layer may be further provided between a cathode and the electron transfer layer.

In one embodiment of the present specification, the photoactive layer comprises one, two or more selected from the group consisting of electron donors and acceptors, and the electron donor material comprises the compound.

In one embodiment of the present specification, the electron acceptor material may be selected from the group consisting of fullerene, fullerene derivatives, bathocuproine, semiconducting elements, semiconducting compounds and combinations thereof. Specifically, one, two or more compounds selected from the group consisting of fullerene, fullerene derivatives ((6,6)-phenyl-C61-butyric acid-methyl ester (PCBM) or (6,6)-phenyl-C61-butyric acid-cholesteryl ester (PCBCR)), perylene, polybenzimidazole (PBI), and 3,4,9,10-perylene-tetracarboxylic bis-benzimidazole (PTCBI) may be comprised.

In one embodiment of the present specification, the electron donor and the electron acceptor forms a bulk heterojunction (BHJ).

A bulk heterojunction means an electron donor material and an electron acceptor material being mixed together in a photoactive layer.

In one embodiment of the present specification, the photoactive layer has a bilayer structure comprising an n-type organic material layer and a p-type organic material layer, and the p-type organic material layer comprises the compound.

The substrate in the present specification may comprise a glass substrate or a transparent plastic substrate having excellent transparency, surface smoothness, handling easiness and water resistance, but is not limited thereto, and substrates typically used in organic solar cells may be used without limit. Specific examples thereof comprise glass, polyethylene teraphthalate (PET), polyethylene naphthalate (PEN), polypropylene (PP), polyimide (PI), triacetyl cellulose (TAC) and the like, but are not limited thereto.

The anode electrode may comprise a material that is transparent and has excellent conductivity, but the material is not limited thereto. Examples of the anode material comprise metals such as vanadium, chromium, copper, zinc or gold, or alloys thereof; metal oxides such as zinc oxides, indium oxides, indium tin oxides (ITO) or indium zinc oxides (IZO); and a combination of metals and oxides such as $ZnO:Al$ or $SnO_2:Sb$; conductive polymers such as poly (3-methylthiophene), poly[3,4-(ethylene-1,2-dioxy)thiophene] (PEDOT), polypyrrole and polyaniline, and the like, but are not limited thereto.

A method of forming the anode electrode is not particularly limited, however, the anode electrode may be formed by being applied to one surface of a substrate or coated in the form of a film using a method such as sputtering, E-beam, thermal deposition, spin coating, screen printing, ink jet printing, doctor blade or gravure printing.

When the anode electrode is formed on a substrate, the result may go through processes of cleaning, dehydrating and modifying to be hydrophilic.

For example, after a patterned ITO substrate is cleaned with a cleaning agent, acetone and isopropyl alcohol (IPA) in consecutive order, the ITO substrate is dried for 1 minute to 30 minutes at 100° C. to 150° C., preferably for 10 minutes at 120° C., on a heating plate in order to dehydrate, and when the substrate is completely cleaned, the surface of the substrate is modified to be hydrophilic.

Through the surface modification such as above, the junctional surface potential may be maintained at a level suitable for the surface potential of a photoactive layer. In addition, when a surface is modified, a polymer thin film may be readily formed on an anode electrode, and the quality of the thin film may be improved.

Preprocessing technologies for an anode electrode comprise a) a surface oxidation method using parallel plate discharge, b) a method of oxidizing the surface through ozone generated by UV rays in a vacuum state, and c) an oxidation method using oxygen radicals generated by plasma.

One of the methods described above may be selected depending on the condition of an anode electrode or a substrate. However, it is commonly preferable to prevent the leave of oxygen on the surface of an anode electrode or a substrate and to suppress the remaining of moisture and organic materials as much as possible, no matter which method is used. In this case, practical effects of the preprocessing may be maximized.

As a specific example, a method of oxidizing the surface through ozone generated by UV rays may be used. Herein, a patterned ITO substrate may be fully dried by baking the patterned ITO substrate on a hot plate after being ultrasonic cleaned, and the patterned ITO substrate is introduced into a chamber and then may be cleaned by the ozone generated by reacting oxygen gas with UV light using a UV lamp.

However, the method of surface modification of the patterned ITO substrate in the present specification is not particularly limited, and any method oxidizing a substrate may be used.

The cathode electrode may comprise a metal having small work function, but is not limited thereto. Specific examples thereof may comprise metals such as magnesium, calcium, sodium, potassium, titanium, indium, yttrium, lithium, gadolinium, aluminum, silver, tin and lead, or alloys thereof; or multilayer structure materials such as LiF/Al, LiO$_2$/Al, LiF/Fe, Al:Li, Al:BaF$_2$ and Al:BaF$_2$:Ba, but are not limited thereto.

The cathode electrode may be formed by being deposited inside a thermal depositor having a vacuum degree of 5×10$^{-7}$ torr or less, but the formation is not limited to this method.

The hole transfer layer and/or the electron transfer layer material play a role of efficiently transferring the electrons and the holes separated in a photoactive layer to an electrode, and the material is not particularly limited.

The hole transfer layer material may comprise poly(3,4-ethylenediocythiophene) doped with poly(styrenesulfonic acid) (PEDOT:PSS), molybdenum oxides (MoO$_x$); vanadium oxide (V$_2$O$_5$); nickel oxide (NiO); tungsten oxides (WO$_x$) and the like, but is not limited thereto.

The electron transfer layer material may comprise electron-extracting metal oxides, and may specifically comprise a metal complex of 8-hydroxyquinoline; a complex comprising Alq$_3$; a metal complex comprising Liq; LiF; Ca; titanium oxides (TiO$_x$); zinc oxide (ZnO); cesium carbonate (Cs$_2$CO$_3$), and the like, but is not limited thereto.

The photoactive layer may be formed by dissolving a photoactive material such as an electron donor and/or an electron acceptor in an organic solvent, and then applying the solution using a method such as spin coating, dip coating, screen printing, spray coating, doctor blade and brush painting, but the method is not limited thereto.

Hereinafter, a method for preparing the compound and a method for manufacturing an organic solar cell comprising the same will be described in detail with reference to the following preparation examples and examples. However, the following examples are for illustrative purposes only, and the scope of the present specification is not limited thereto.

Preparation Example 1. Preparation of Compound A-1

(1) Preparation of Compound 1-b

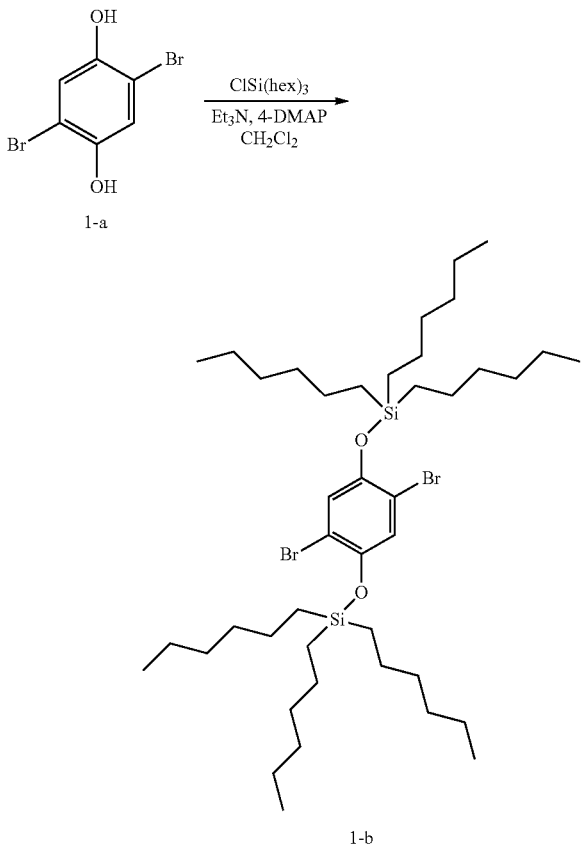

After dissolving 1-a (2 g, 7.47 mmol) and 4-dimethylaminopyridine (0.36 g, 2.92 mmol) in 30 mL of chloroform and lowering the temperature to 0° C., triethylamine (3 mL, 21.51 mmol) and chloro(trihexyl) (7.46 mL, 20.37 mmol) were injected thereto, and the result was stirred for 12 hours at room temperature. After the reaction, the reactant was introduced to 100 mL of water, and extracted with dichloromethane. After that, residual water was removed using magnesium sulfate, and then the solvent was removed under vacuum. A residual product was purified using silica column (hexane:dichloromethane) to obtain transparent oil 1-b. (Yield: 94%)

Figure 2:
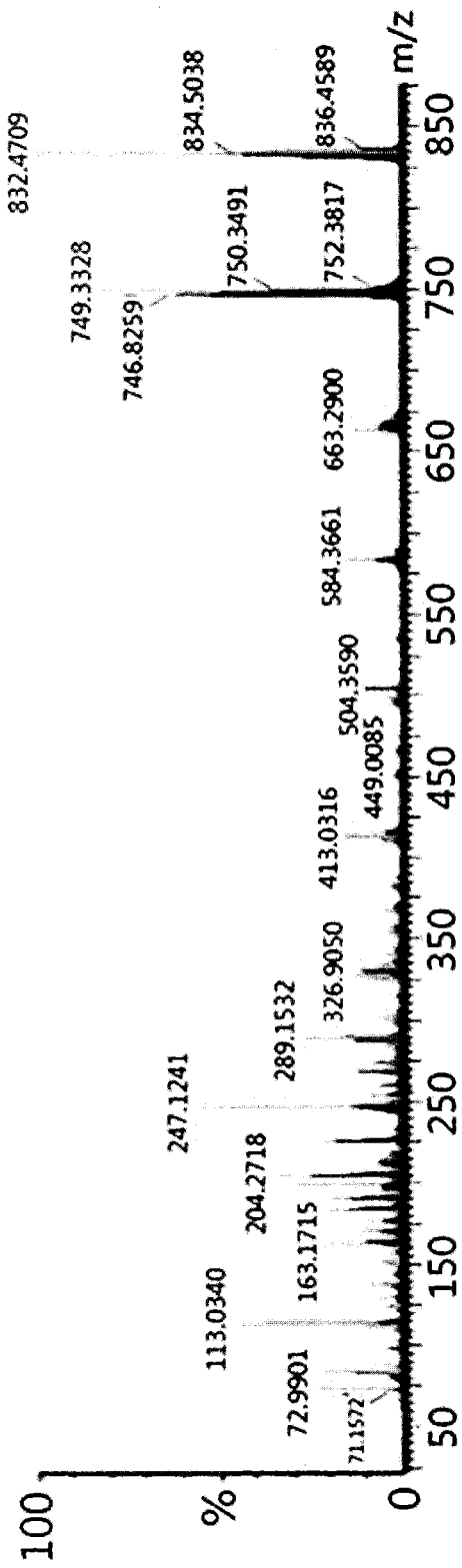
FIG. 2 is a diagram showing an MS spectrum of Compound 1-b.

FIG. 2 is a diagram showing an MS spectrum of Compound 1-b.

Figure 3:
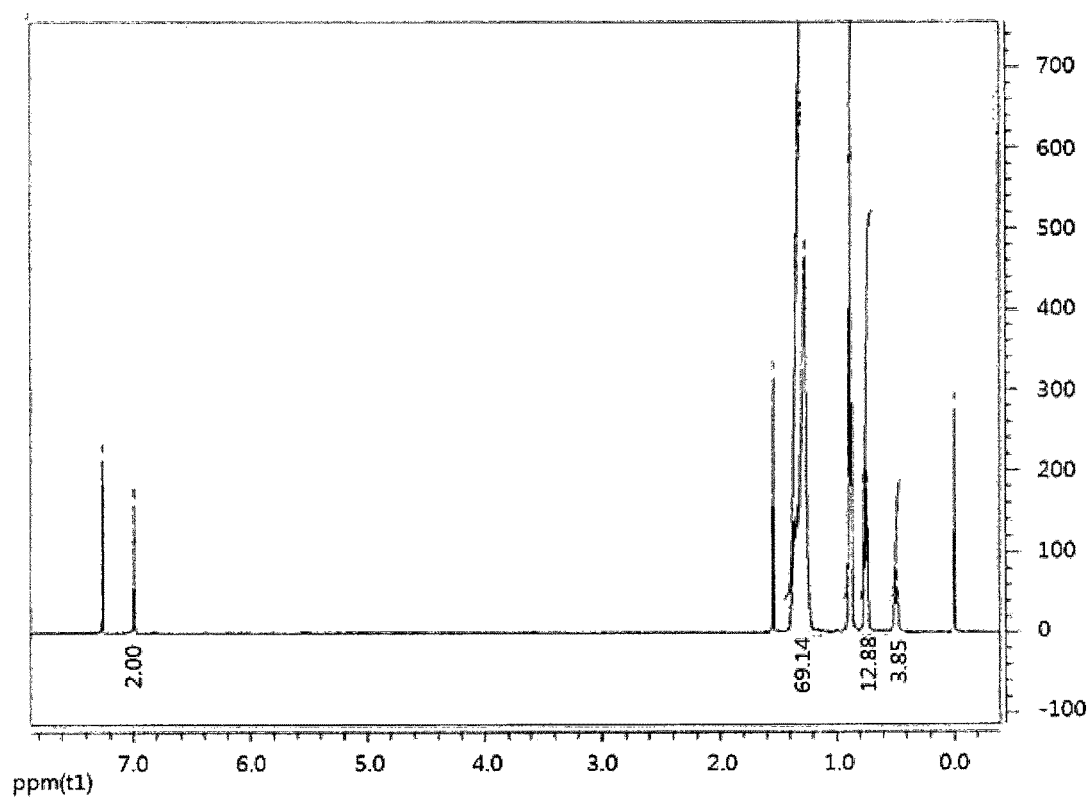
FIG. 3 is a diagram showing an NMR spectrum of Compound 1-b.

FIG. 3 is a diagram showing an NMR spectrum of Compound 1-b.

(2) Preparation of Compound A

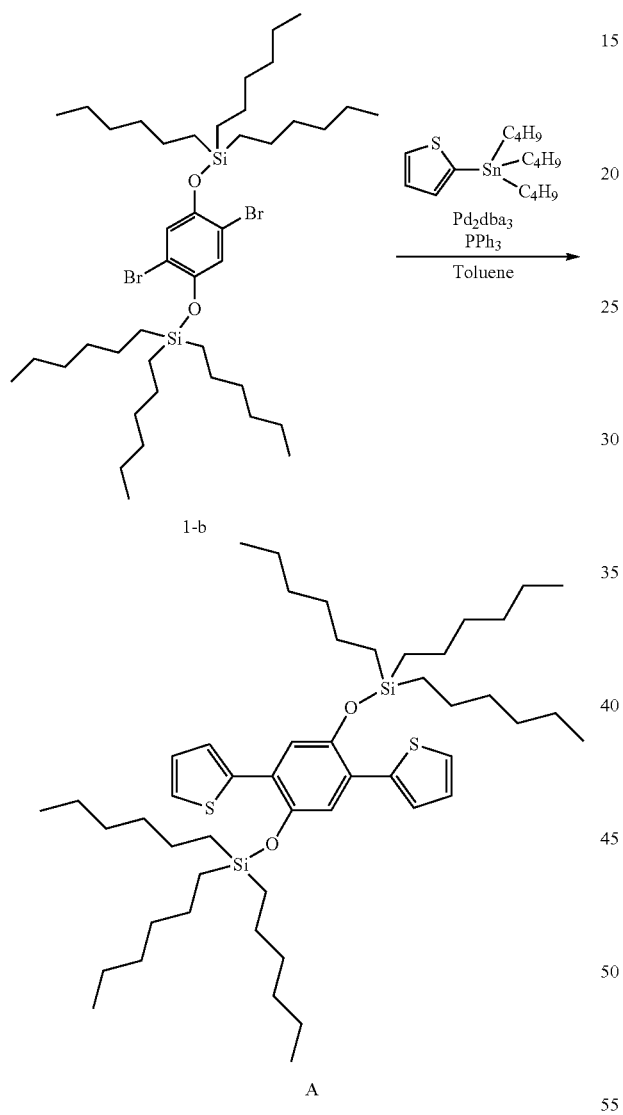

After dissolving 1-b (5 g, 6 mmol) and tributyltin-thiophene (9.33 g, 25 mmol) in 70 mL of toluene, a tris(dibenzylideneacetone)dipalladium(0) catalyst (0.458 g, 0.5 mmol) and a triphenylphosphine ligand (0.52 g, 2 mmol) were added thereto, and the result was stirred for 48 hours at 110° C. After the reaction, the reactant was extracted with dichloromethane. After that, residual water was removed using magnesium sulfate, and then the solvent was removed under vacuum. A residual product was purified using silica column (hexane:dichloromethane) to obtain transparent oil A. (Yield: 59%)

Figure 4:
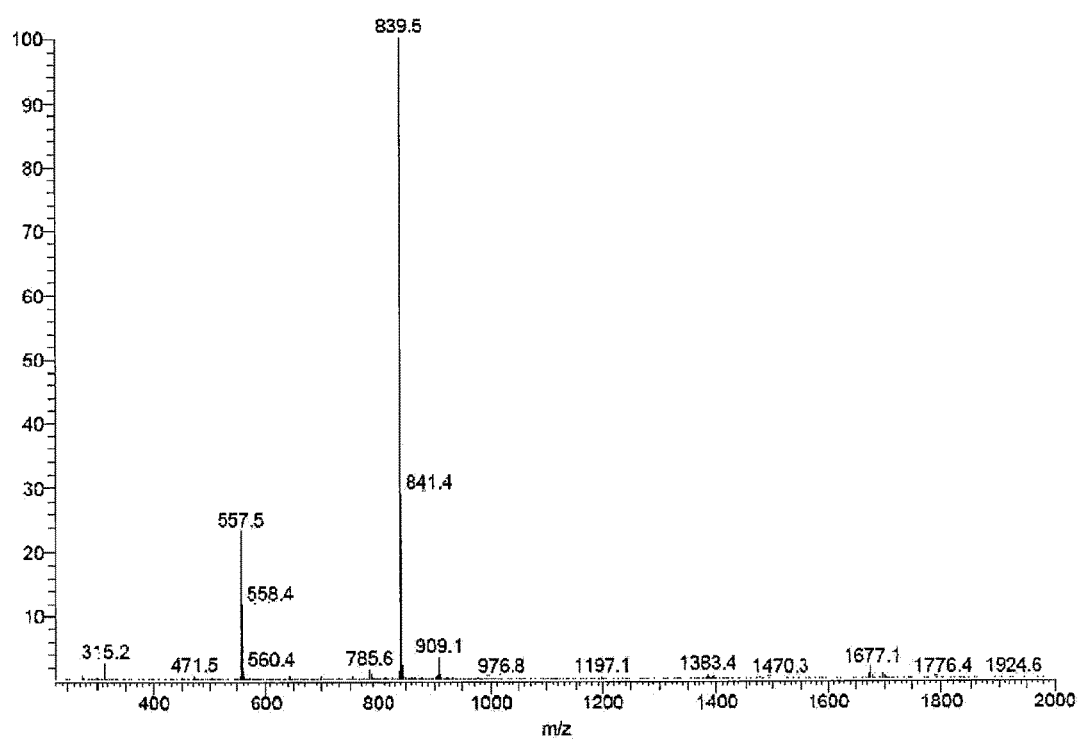
FIG. 4 is a diagram showing an MS spectrum of Compound A.

FIG. 4 is a diagram showing an MS spectrum of Compound A.

Figure 5:
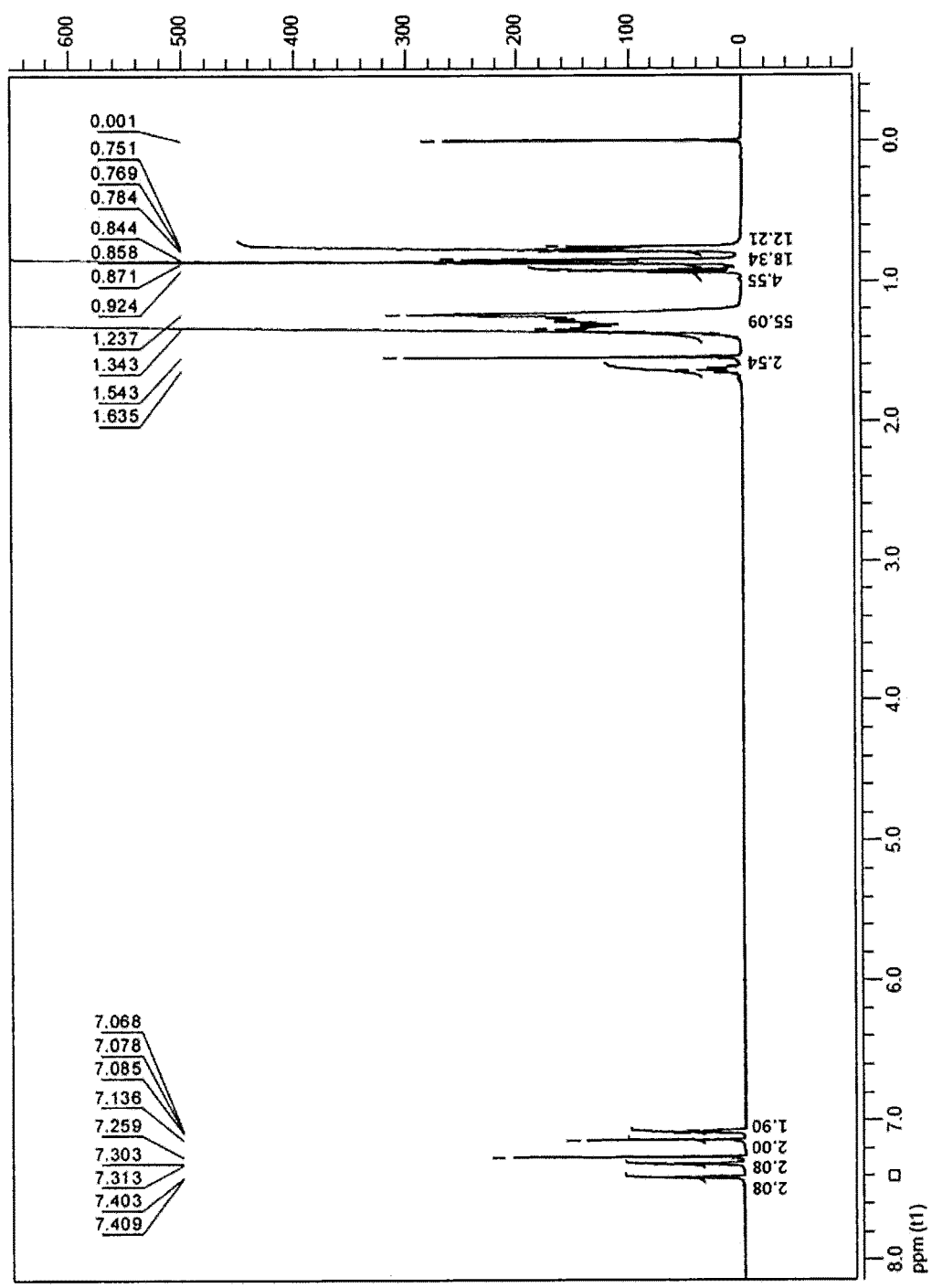
FIG. 5 is a diagram showing an NMR spectrum of Compound A.

FIG. 5 is a diagram showing an NMR spectrum of Compound A.

(3) Preparation of Compound A-1

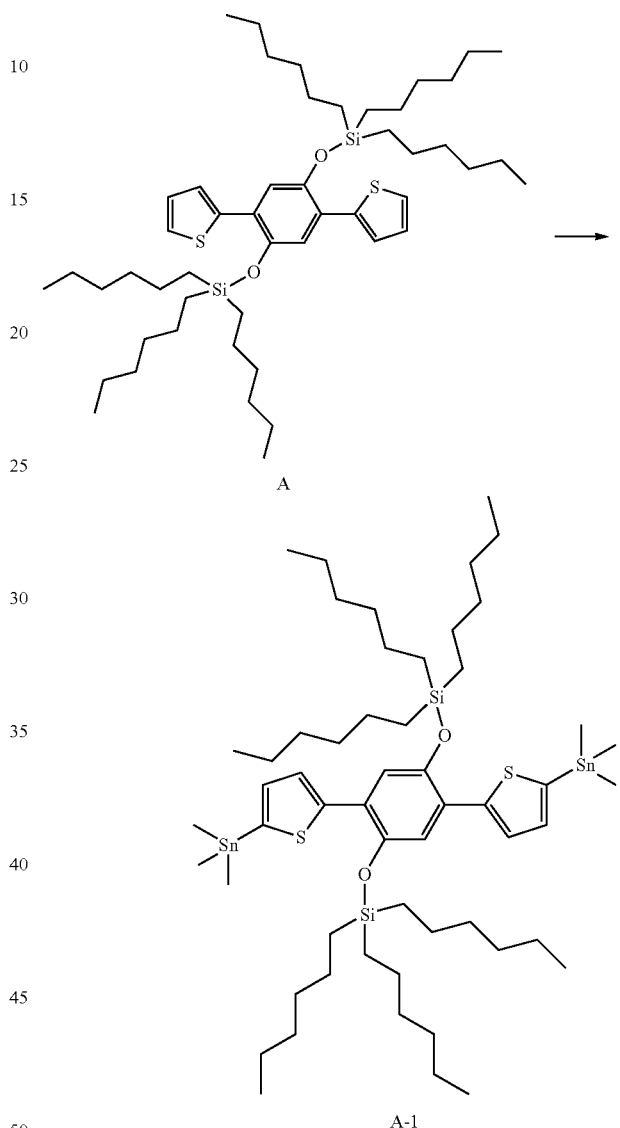

After dissolving A (3.0 g, 3.55 mmol) in 100 mL of tetrahydrofuran, 2 M lithium diisopropylamide (5.325 mL, 10.65 mmol) was slowly injected thereto at −78° C., and the result was stirred for 2 hours at −78° C. At the same temperature, trimethyltin chloride (11 mL, 11 mmol) was introduced thereto, and the temperature was slowly raised to room temperature. This solution was extracted with DCM, residual water was removed using magnesium sulfate ($MgSO_4$), and then the solvent was removed under vacuum. A residual product went through silica column (eluent: n-hexane) to obtain yellow liquid A-1. (Yield: 83%)

Figure 7:
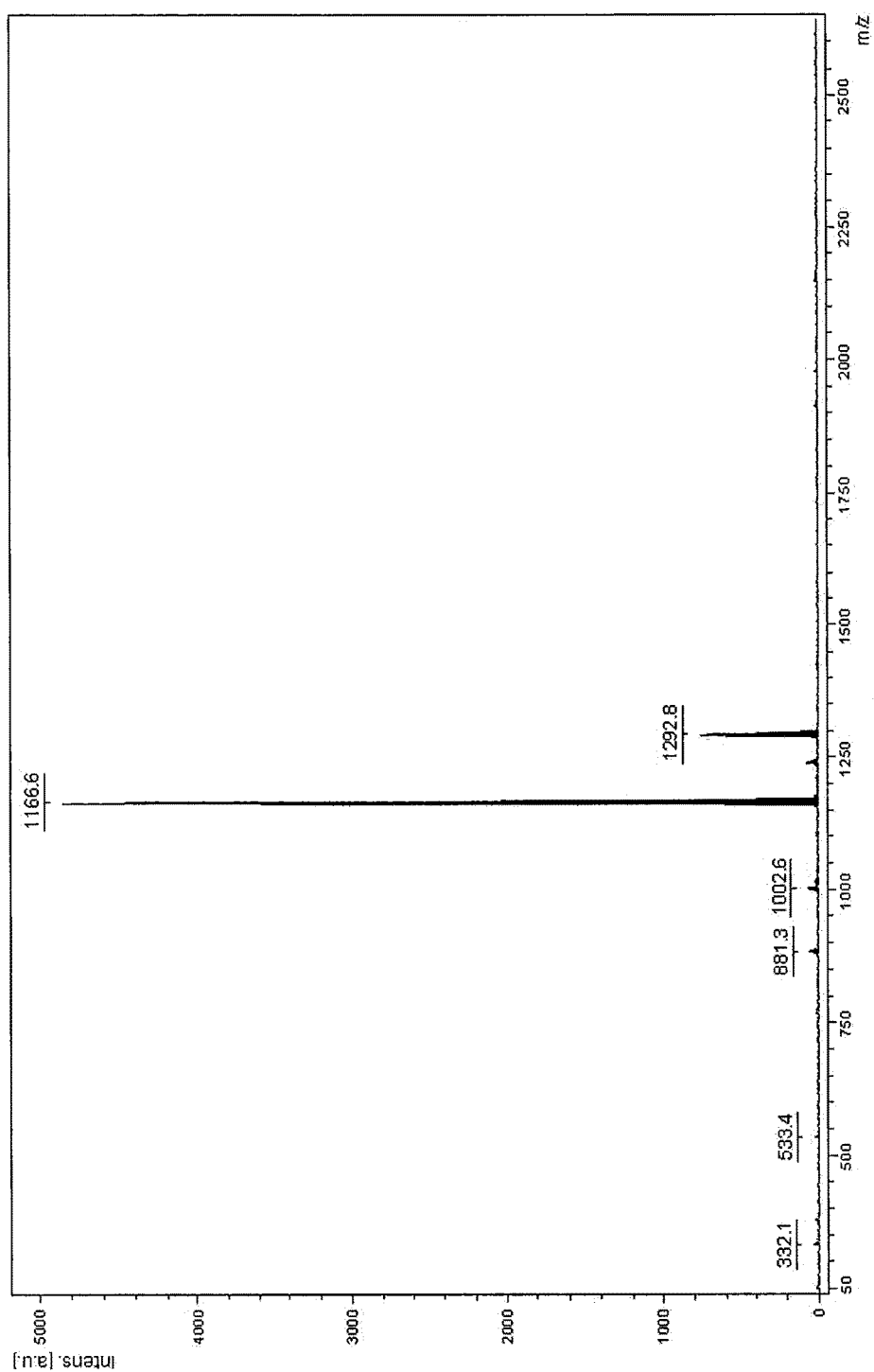
FIG. 7 is a diagram showing an MS spectrum of Compound A-1.

FIG. 7 is a diagram showing an MS spectrum of Compound A-1.

Figure 8:
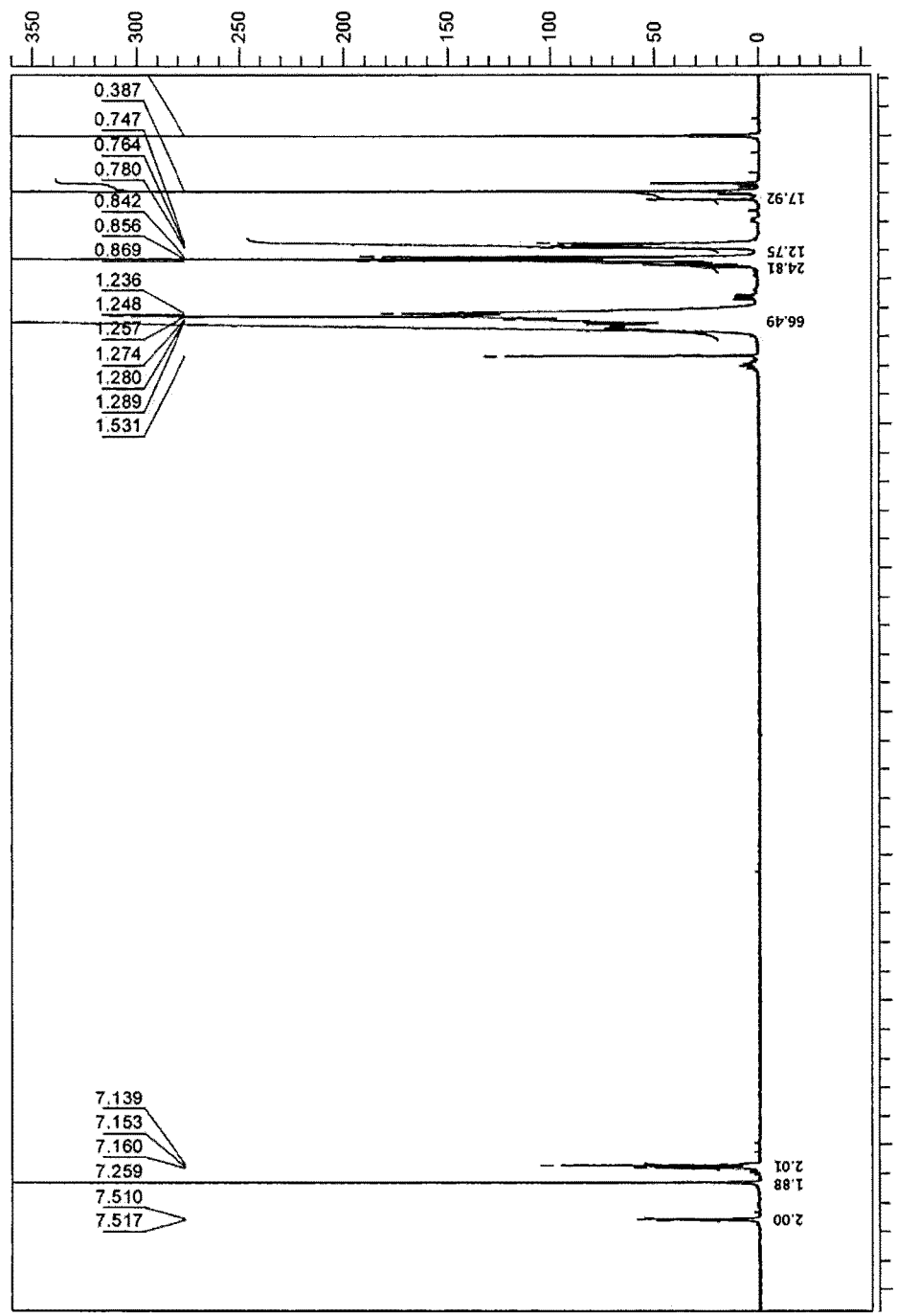
FIG. 8 is a diagram showing an NMR spectrum of Compound A-1.

FIG. 8 is a diagram showing an NMR spectrum of Compound A-1.

(4) Preparation of Compound A-2

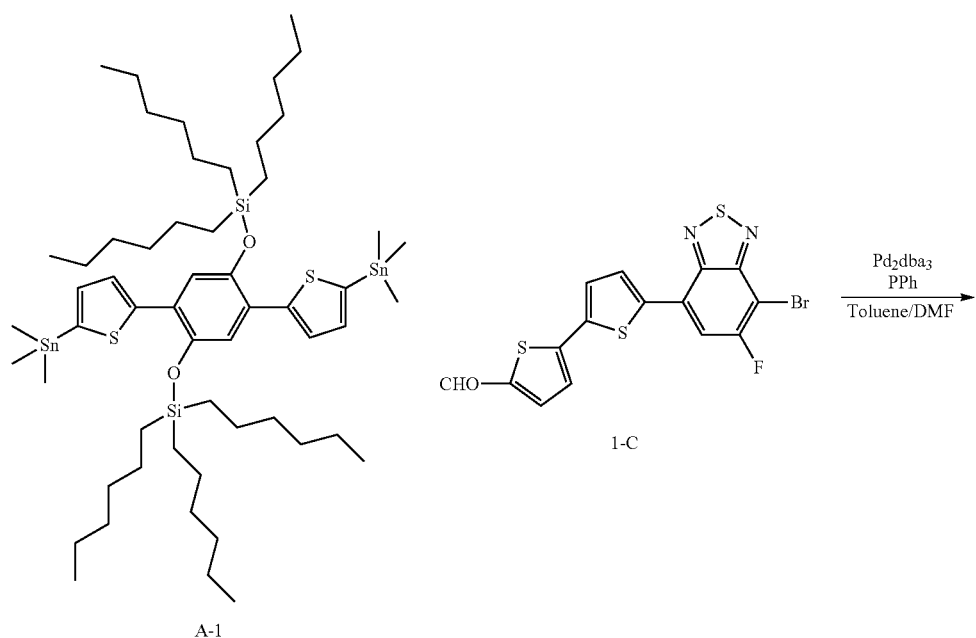

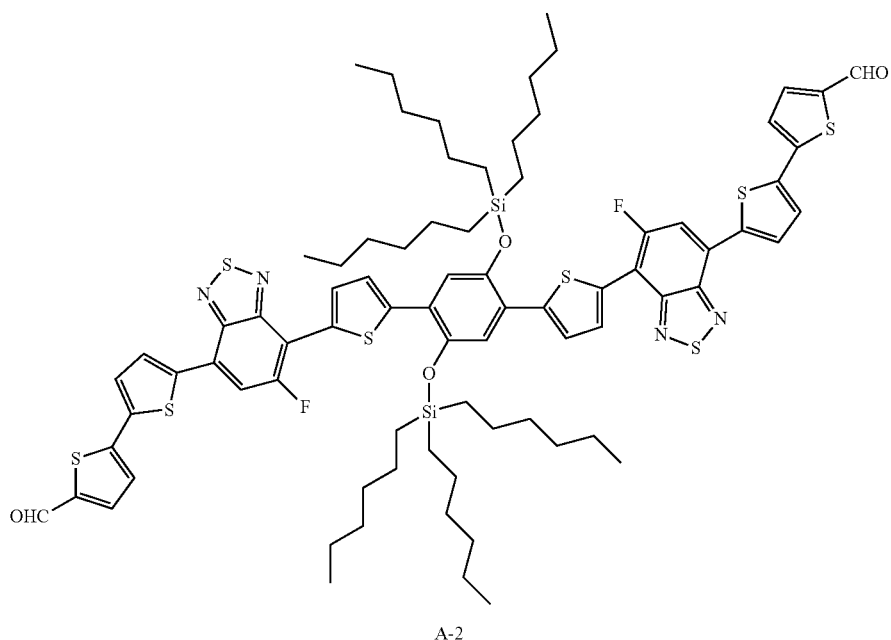

After dissolving 1-c (0.808 g, 1.9 mmol) and A-1 (0.99 g, 0.85 mmol) in 40 mL of toluene and 4 mL of dimethylformamide, a tris(dibenzylideneacetone)dipalladium (0) catalyst (0.0385 g, 0.042 mmol) and a triphenylphosphine ligand (0.0441 g, 0.168 mmol) were added thereto, and the result was stirred for 48 hours at 110° C. After the reaction, this solution was extracted with dichloromethane, residual water was removed using magnesium sulfate ($MgSO_4$), and then the solvent was removed under vacuum. A residual product went through silica column (eluent: chloroform) to obtain red solid A-2. (Yield: 45%)

Figure 9:
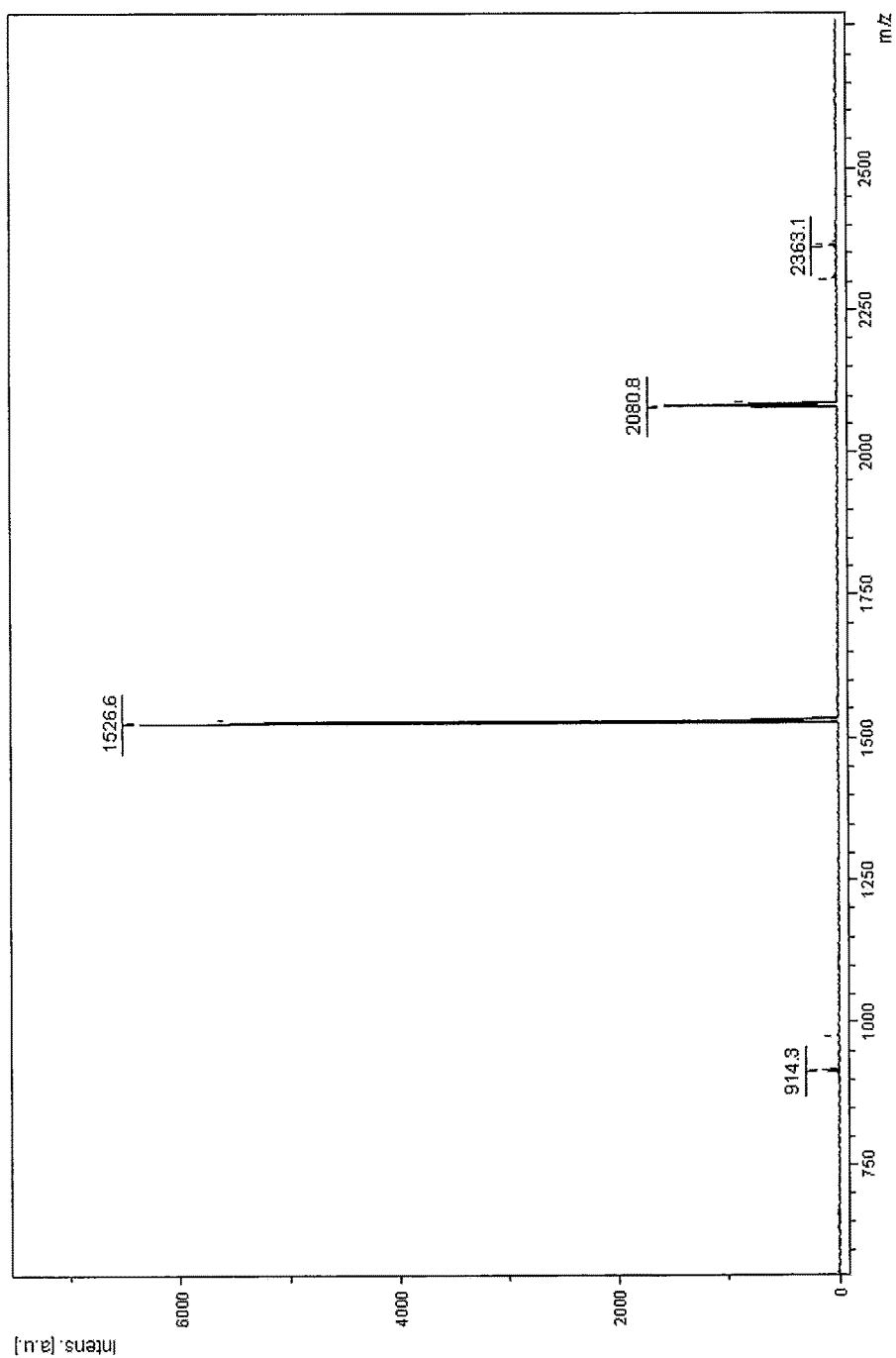
FIG. 9 is a diagram showing an MS spectrum of Compound A-2.

FIG. 9 is a diagram showing an MS spectrum of Compound A-2.

Figure 10:
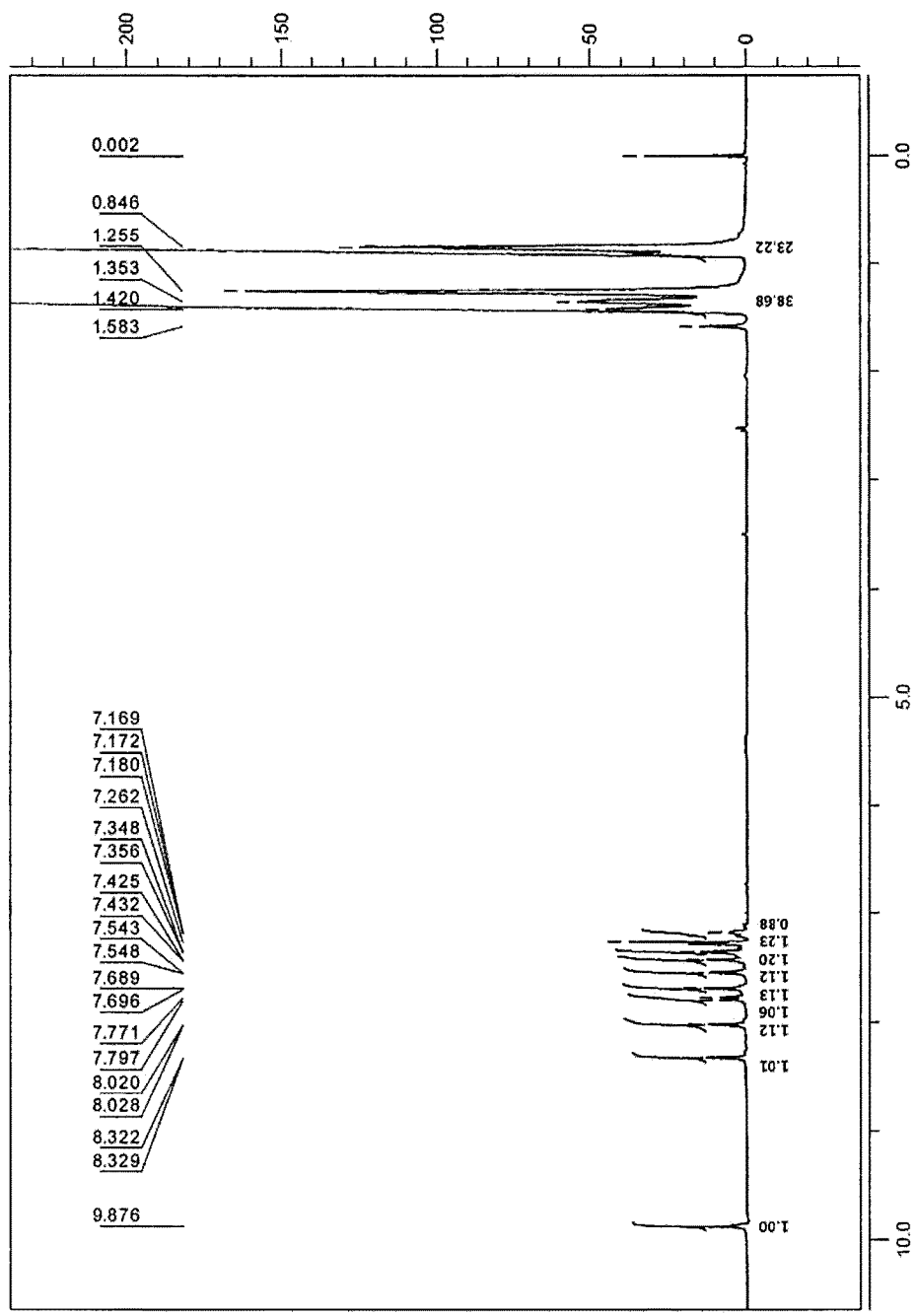
FIG. 10 is a diagram showing an NMR spectrum of Compound A-2.

FIG. 10 is a diagram showing an NMR spectrum of Compound A-2.

Preparation Example 2. Preparation of Compound A-3

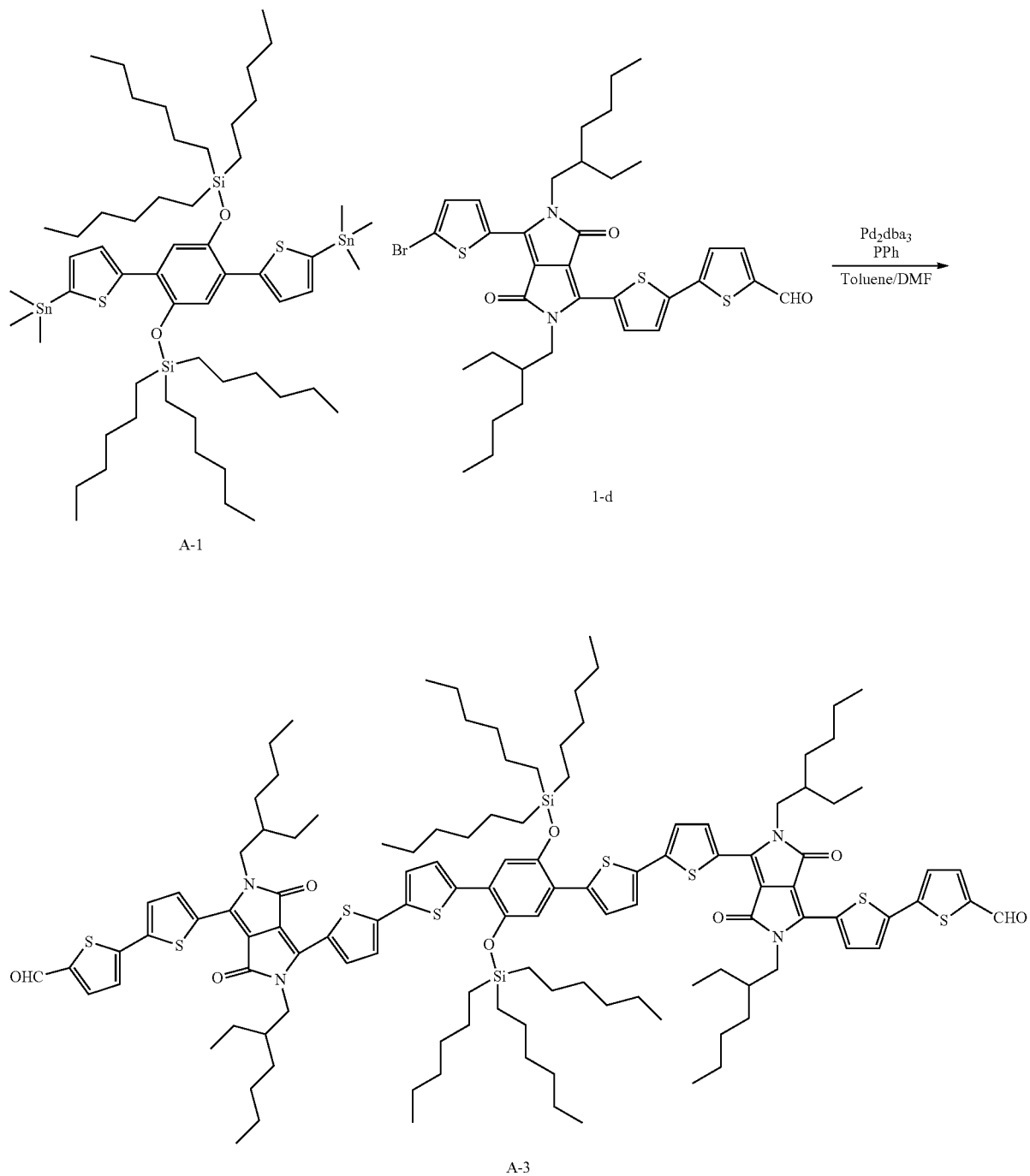

After dissolving DPP (1.48 g, 2.08 mmol) and A-1 (0.93 g, 0.80 mmol) in 30 mL of toluene and 10 mL of dimethylformamide, a tetrakis(triphenylphosphine)palladium(0) catalyst (0.0289 g, 0.025 mmol) was added thereto, and the result was stirred for 48 hours at 110° C. After the reaction, this solution was extracted with dichloromethane, residual water was removed using magnesium sulfate ($MgSO_4$), and then the solvent was removed under vacuum. A residual product went through silica column (eluent: chloroform) to obtain red solid A-3. (Yield: 49%)

Figure 11:
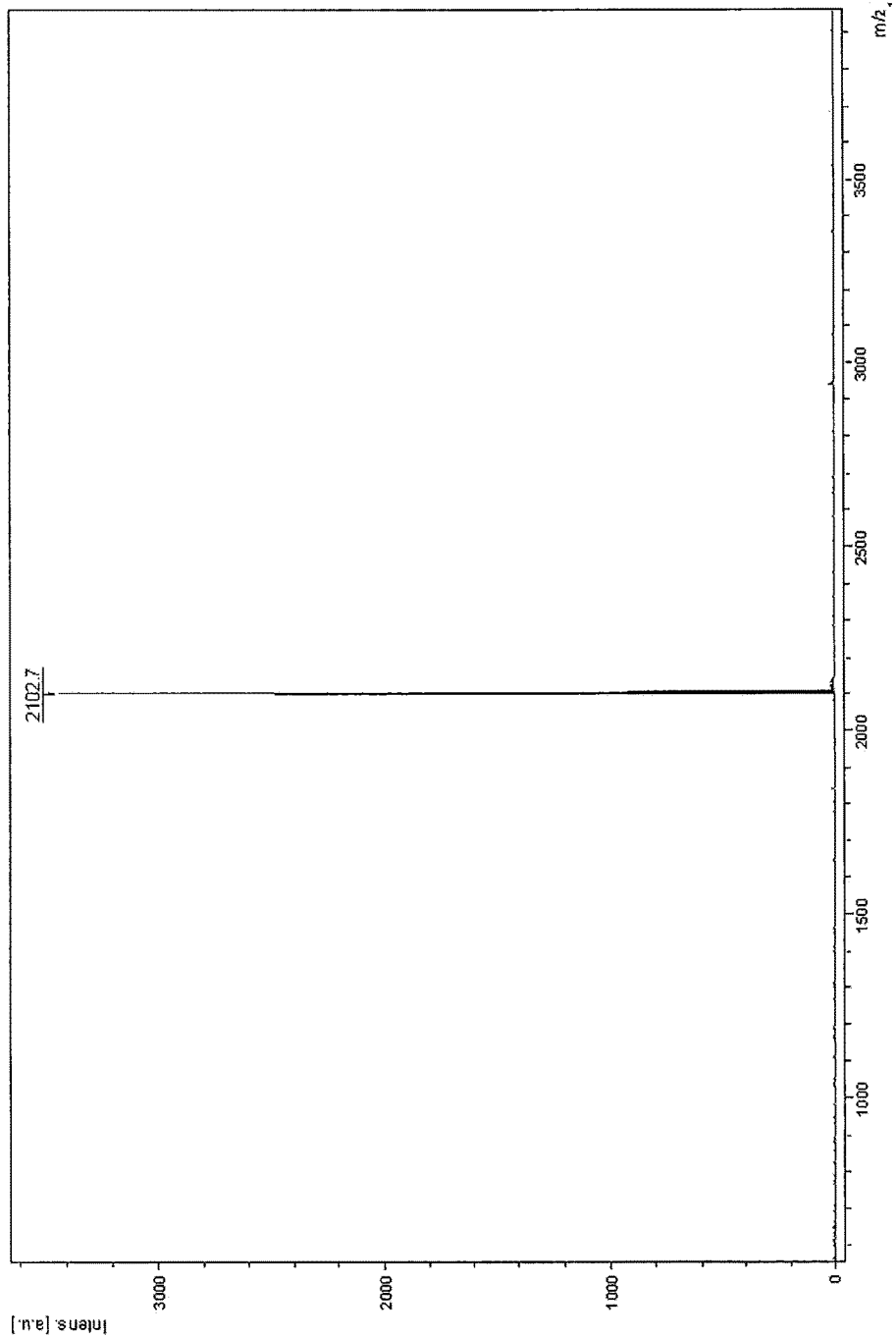
FIG. 11 is a diagram showing an MS spectrum of Compound A-3.

FIG. 11 is a diagram showing an MS spectrum of Compound A-3.

Figure 12:
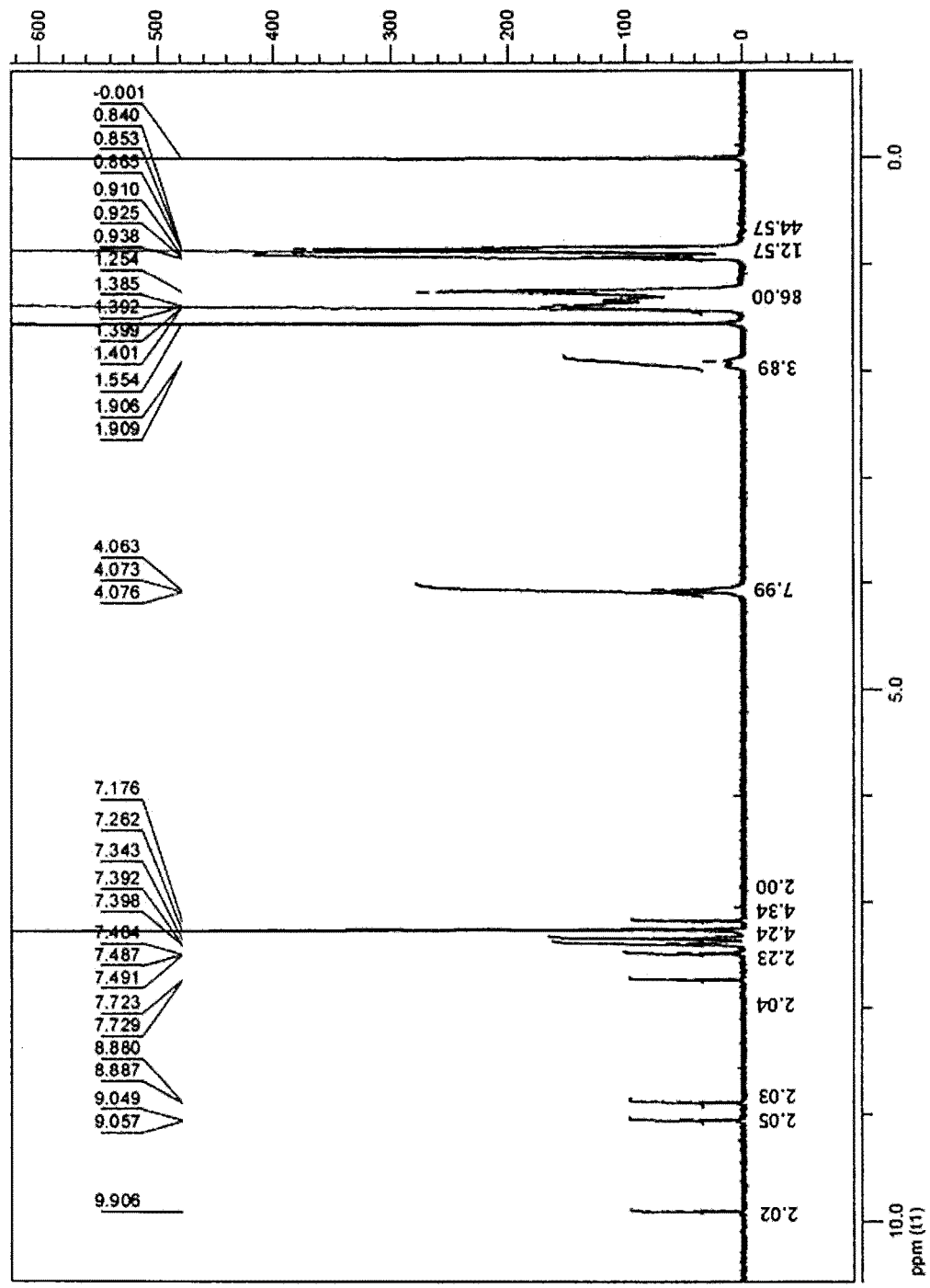
FIG. 12 is a diagram showing an NMR spectrum of Compound A-3.

FIG. 12 is a diagram showing an NMR spectrum of Compound A-3.

Preparation Example 3. Preparation of Compound B (1) Preparation of Compound 2-b

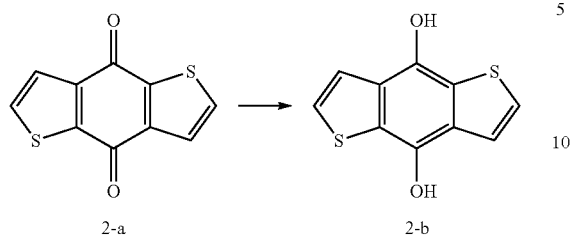

2-a    2-b

While stirring suspension adding 2-a (13.95 g, 0.063 mmol) to 200 mL of ethanol and cooling the result in an ice/water bath, NaBH$_4$ (5.27 g, 0.139 mmol) were added thereto at once. The reactant was stirred for 3 hours at room temperature. After that, 250 mL of HCl was poured thereto to terminate the reaction, and then a crude product was filtered, washed with a sufficient amount of water, and vacuum dried at 70° C. After the drying, green solid 2-b was obtained. (Yield: 98%)

Figure 6:
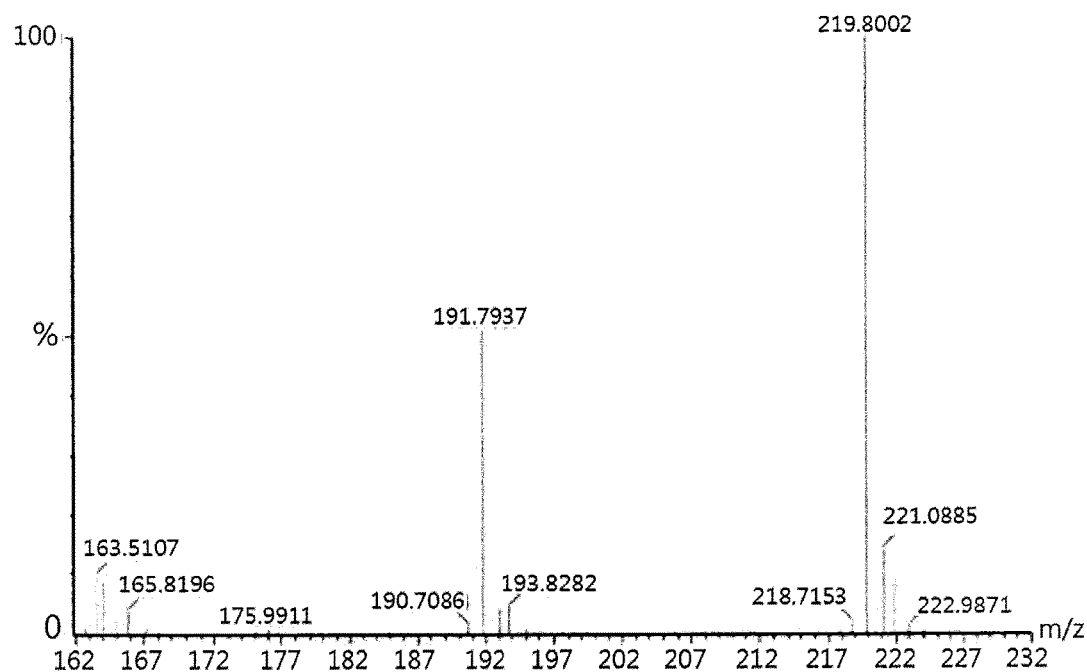
FIG. 6 is a diagram showing an MS spectrum of Compound 2-b.

FIG. 6 is a diagram showing an MS spectrum of Compound 2-b.

(2) Preparation of Compound B

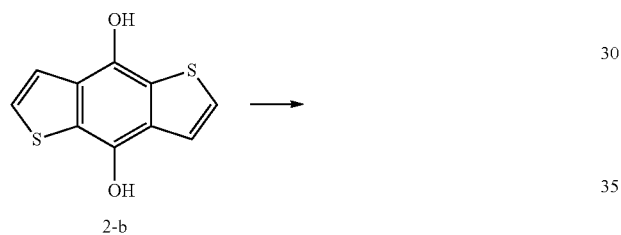

2-b

A compound was prepared in the same manner as in Preparation Example 1 except that 2-b was used instead of 1-b.

Preparation Example 4. Preparation of Compound 1

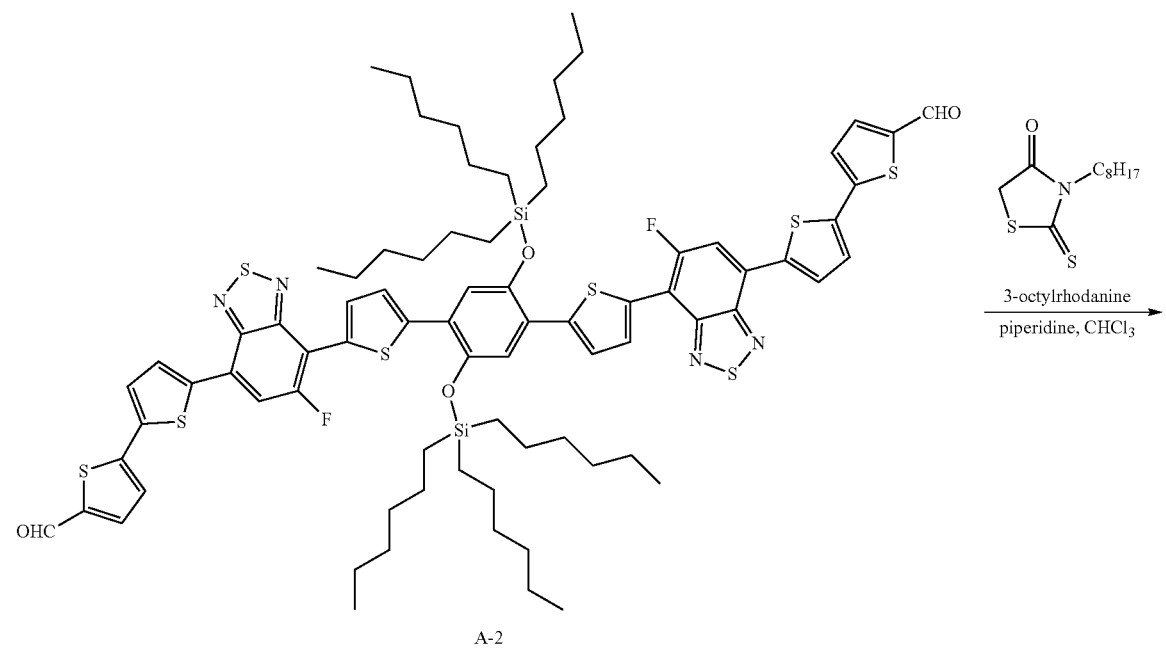

A-2

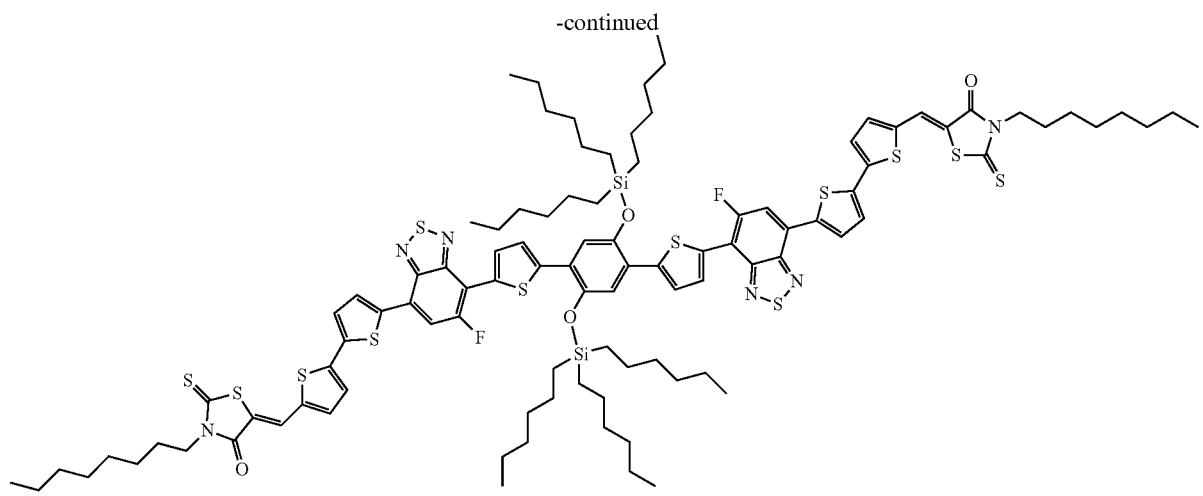

After dissolving Compound A-2 (0.153 g, 0.1 mmol) and 3-octylrhodanine (0.245 g, 1 mmol) in 40 mL of CHCl₃, three drops of piperidine was added thereto at room temperature, and the result was refluxed for 24 hours. After the reaction, the reactant was extracted with DCM, residual water was removed using MgSO₄, and the solvent was removed under vacuum. A residual product went through silica column (eluent: CHCl₂ to CHCl₃) to obtain dark brown solid. The obtained solid was recrystallized three times using CHCl₃ and n-hexane to obtain Compound 1. (Yield: 56%)

Figure 13:
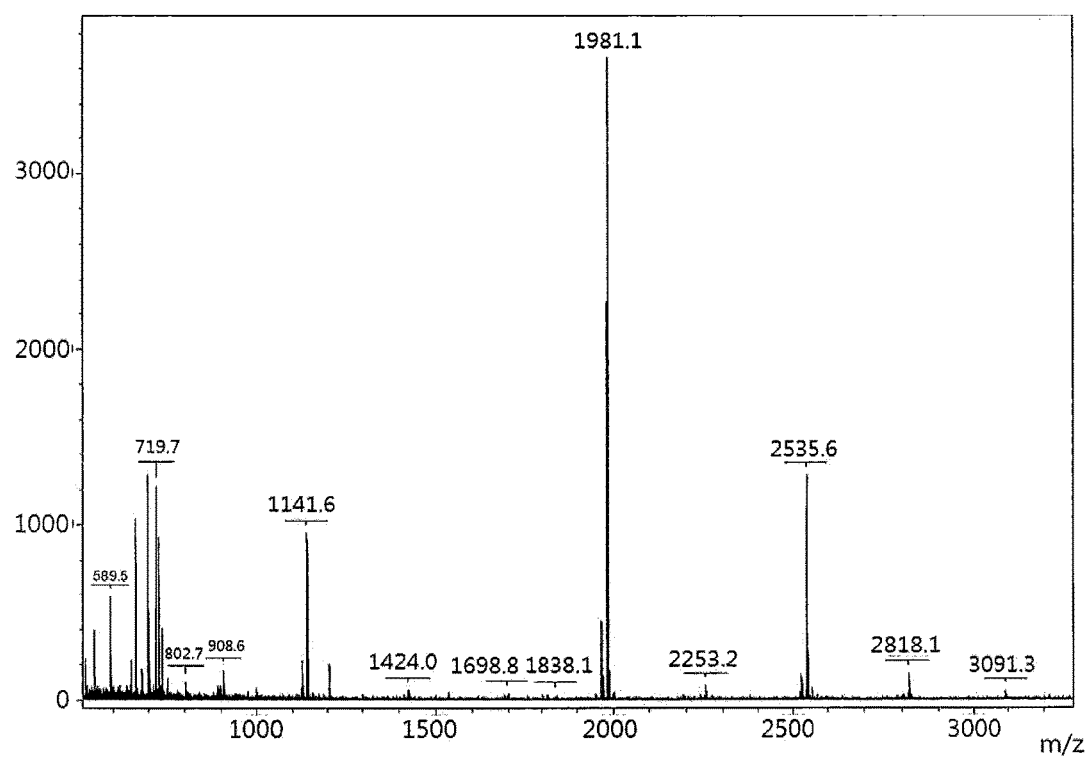
FIG. 13 is a diagram showing an MS spectrum of Compound 1.

FIG. 13 is a diagram showing an MS spectrum of Compound 1.

Preparation Example 5. Preparation of Compound 2

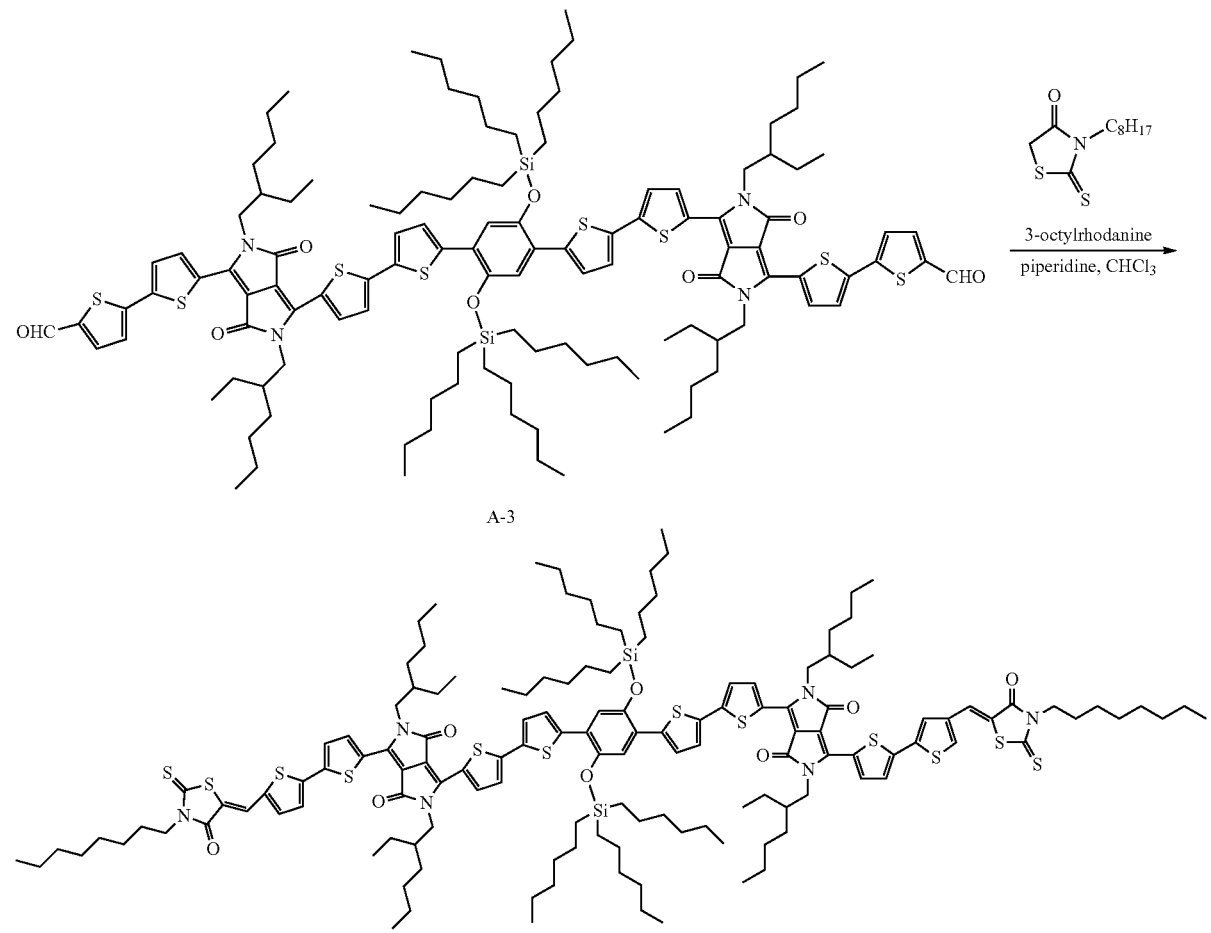

After dissolving Compound A-3 (0.42 g, 0.2 mmol) and 3-octylrhodanine (0.368 g, 1.5 mmol) in 40 mL of CHCl₃, three drops of piperidine was added thereto at room temperature, and the result was refluxed for 24 hours. After the reaction, the reactant was extracted with DCM, residual water was removed using MgSO₄, and the solvent was removed under vacuum. A residual product went through silica column (eluent: CH₂Cl₂ to CHCl₃) to obtain dark brown solid. The obtained solid was recrystallized three times using CHCl₃ and n-hexane to obtain Compound 2. (Yield: 60.5%)

Figure 14:
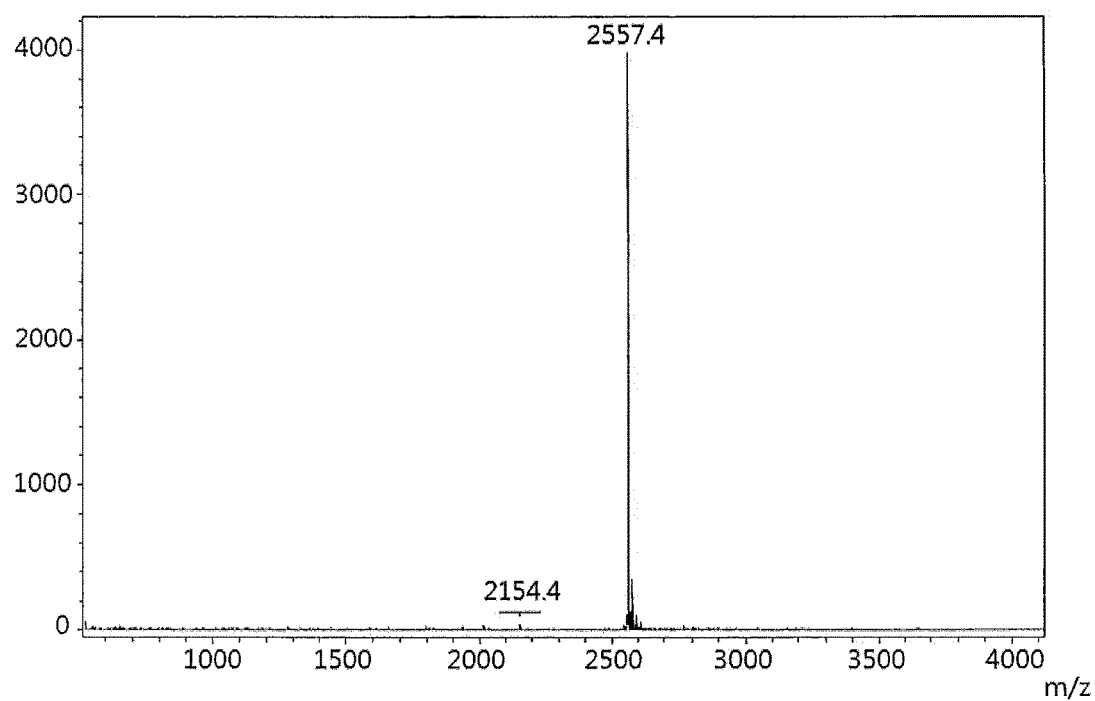
FIG. 14 is a diagram showing an MS spectrum of Compound 2.

FIG. 14 is a diagram showing an MS spectrum of Compound 2.

Figure 15:
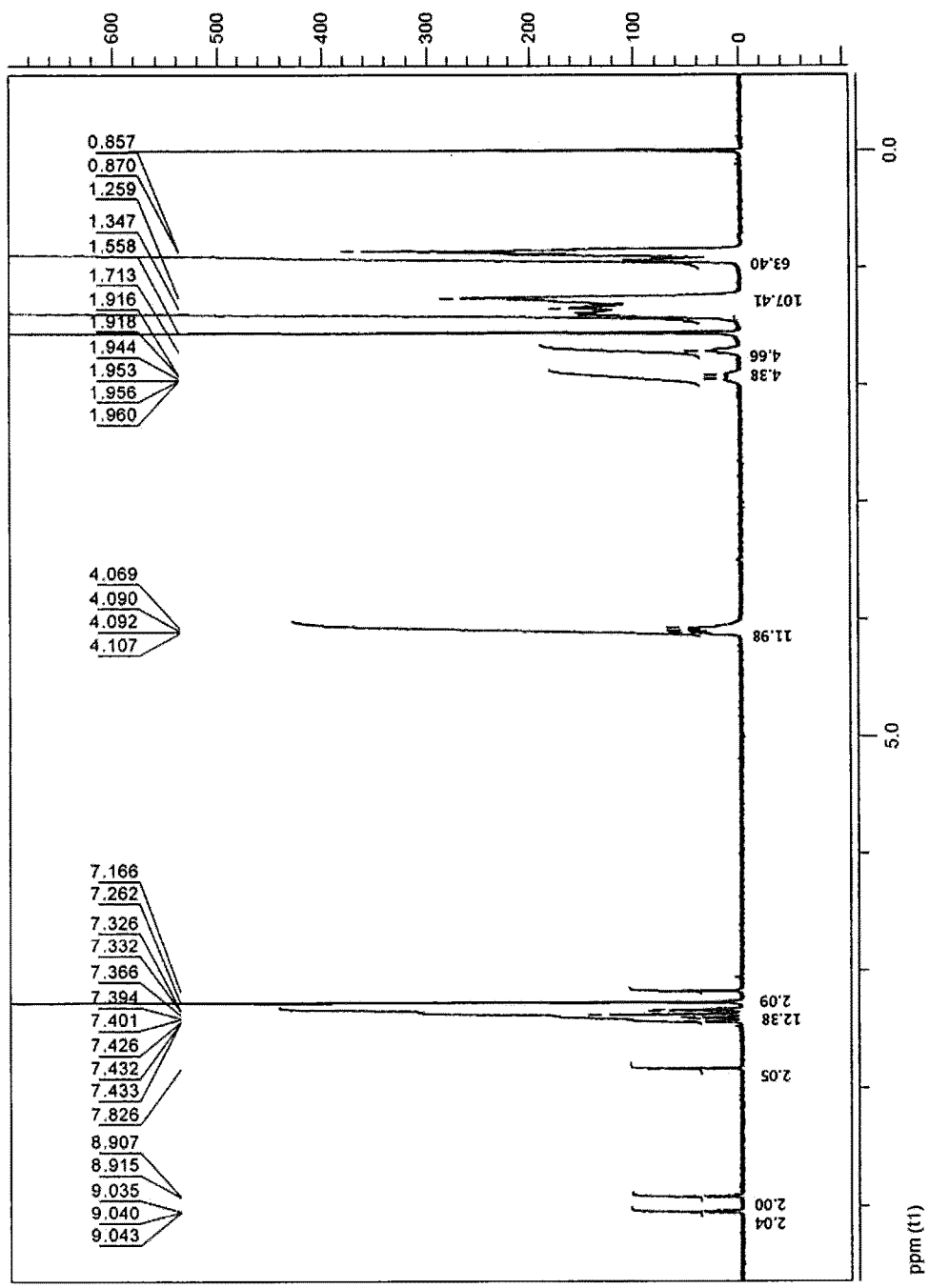
FIG. 15 is a diagram showing an NMR spectrum of Compound 2.

FIG. 15 is a diagram showing an NMR spectrum of Compound 2.

Figure 16:
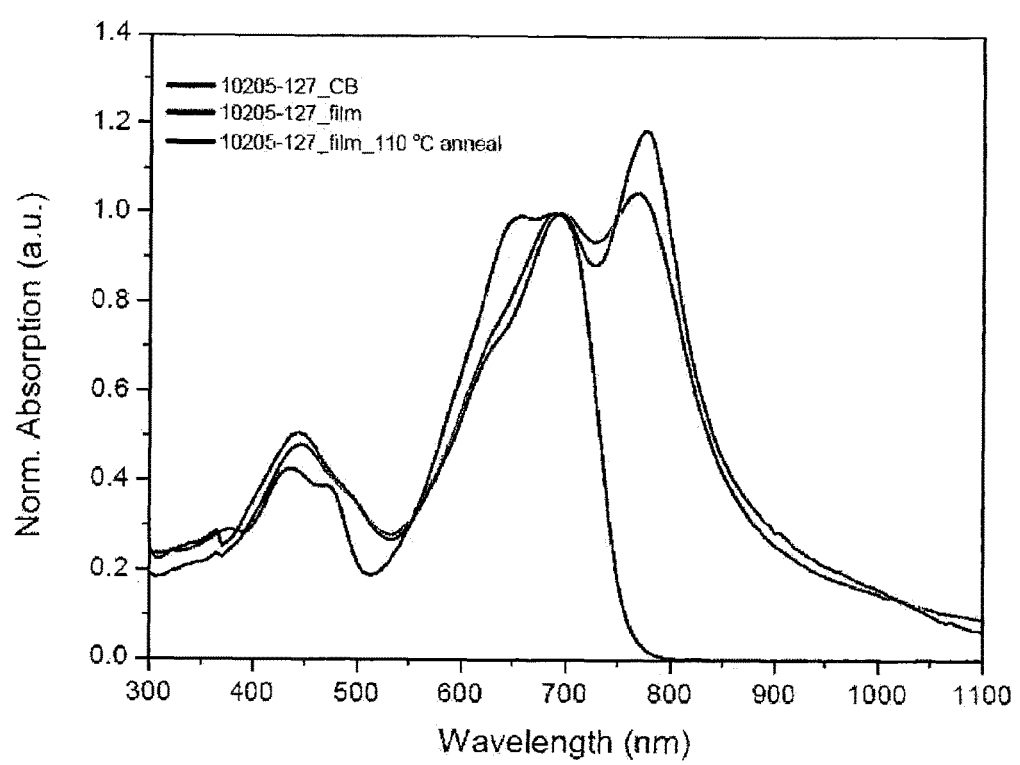
FIG. 16 is a diagram showing a UV-vis absorption spectrum of Compound 2.

FIG. 16 is a diagram showing a UV-vis absorption spectrum of Compound 2.

Specifically, the UV absorption spectrum of FIG. 16 is an absorption spectrum of Compound 2 in a film state and a solution state, and is analyzed using a UV-vis absorption spectrometer, and the results are shown in the following Table 1.

TABLE 1

|  | $\lambda_{max}$ (CB) (nm) | $\lambda_{max}$ (film) (nm) | $\lambda$Op.BG (eV) | $\lambda$Ec.BG (eV) | HOMO (eV) |
|---|---|---|---|---|---|
| Compound 2 | 690 | 770 | 1.38 | 1.47 | 5.20 |

Figure 18:
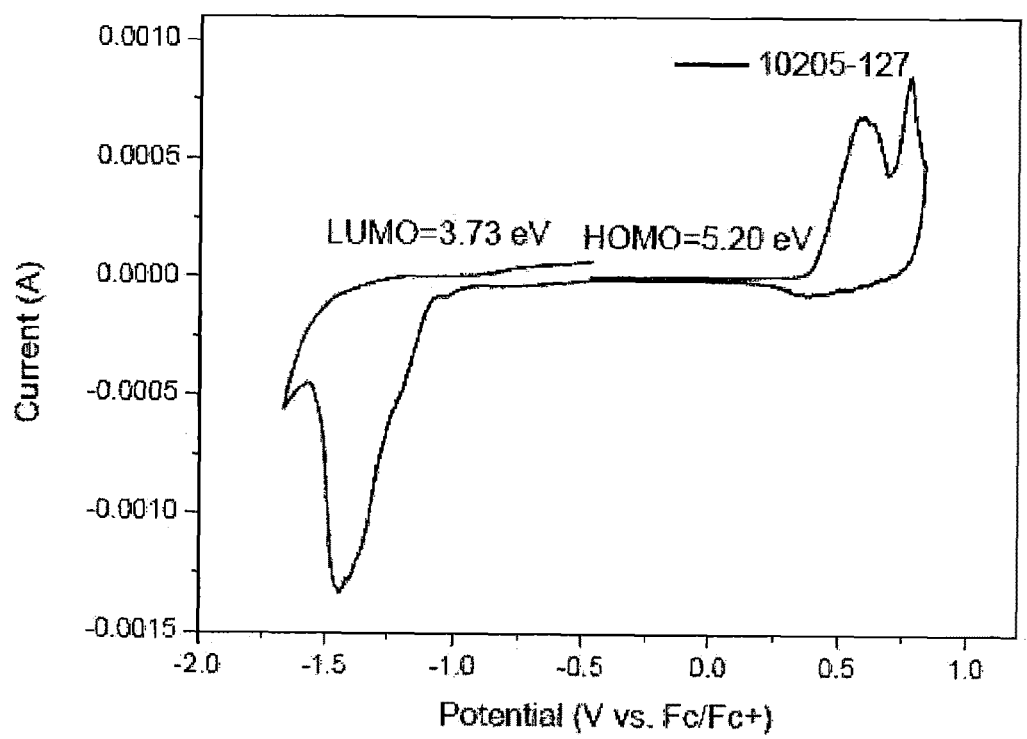
FIG. 18 is a diagram showing a current of Compound 2 depending on potential.

FIG. 18 is a diagram showing current of Compound 2 depending on potential.

Test Example 1. Manufacture of Organic Solar Cell

A composite solution was prepared by dissolving Compound 2 and PC₇₀BM in chlorobenzene (CB) in a ratio of 1:1.25. Herein, the concentration was adjusted to 4.0 wt %, and the organic solar cell employed an inverted structure of ITO/ZnO/photoactive layer/MoO₃/Ag.

A glass substrate in which 1.5 cm²×1.5 cm² was coated with ITO in a bar type was ultrasonic cleaned using distilled water, acetone and 2-propanol, and after the ITO surface was ozone treated for 10 minutes, a zinc oxide (ZnO) precursor solution (ZnO nanoparticle 25 mg/ml in butanol) was prepared, and after spin-coating this zinc oxide (ZnO) solution for 40 seconds at 4000 rpm, heat treatment was carried out for 10 minutes at 100° C. to remove the remaining solvent, and an electron transfer layer was completed. In order to coat a photoactive layer, the composite solution of Compound 2 and PC₇₀BM was spin coated for 20 seconds at 1000 rpm. A hole transfer layer was prepared by depositing MoO₃ to a thickness of 10 nm at a rate of 0.2 Å/s in a thermal depositor. After the preparation in this order, Ag was deposited to 100 nm at a rate of 1 Å/s inside a thermal depositor to manufacture an organic solar cell having an inverted structure.

Photoelectric transformation properties of the organic solar cell manufactured in Test Example 1 were measured under a 100 mW/cm² (AM 1.5) condition, and the results are shown in the following Table 2.

TABLE 2

|  | Voc (V) | Jsc (mA/cm²) | FF (%) | PCE (%) |
|---|---|---|---|---|
| Test Example 1 | 0.81 | 10.78 | 62.7 | 5.47 |

Figure 17:
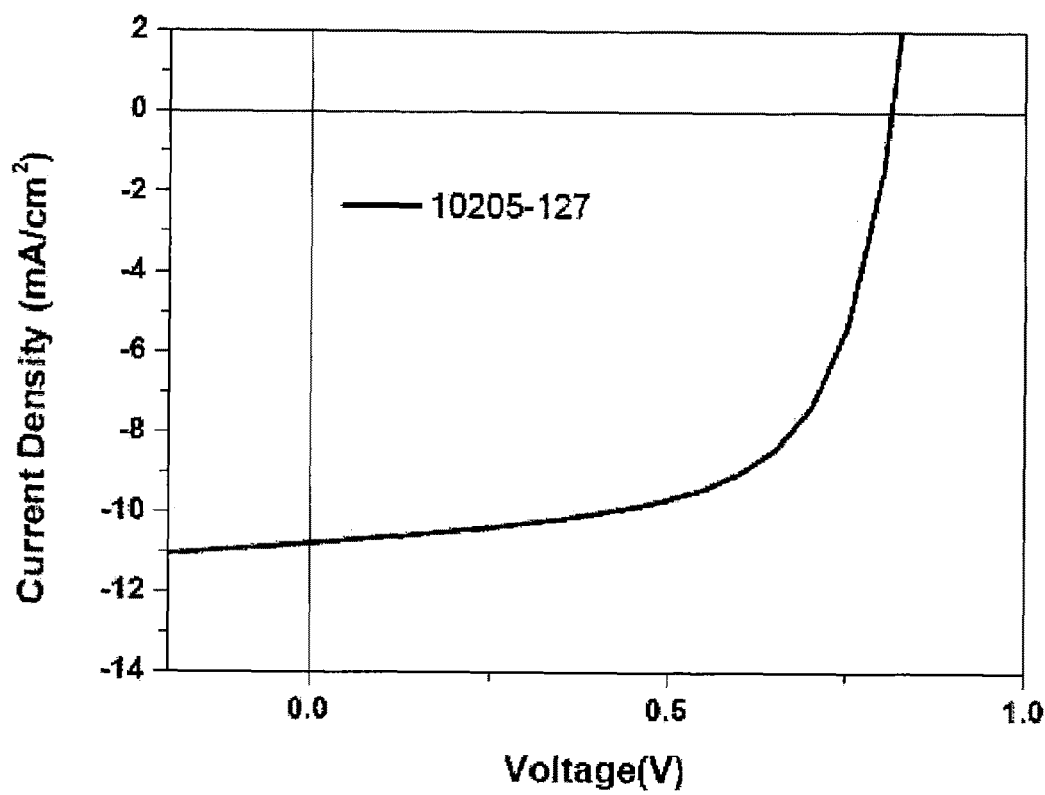
FIG. 17 is a diagram showing current density of an organic solar cell according to Test Example 1 depending on a voltage.

FIG. 17 is a diagram showing current density of the organic solar cell according to Test Example 1 depending on a voltage.

The $V_{oc}$ means an open voltage, the $J_{sc}$ means a short-circuit current, the FF means a fill factor, and the PCE(η) means energy conversion efficiency. The open voltage and the short-circuit current are each an x-axis and a y-axis intercept in the four quadrants of a voltage-current density curve, and as these two values increase, solar cell efficiency is preferably enhanced. In addition, the fill factor is a value dividing the rectangle area that may be drawn inside the curve by the product of the short-circuit current and the open voltage. The energy conversion efficiency may be obtained when these three values are divided by the irradiated light, and it is preferred as the value is higher. Based on the results of Table 2, it was identified that the polymer according to one embodiment of the present specification exhibited high efficiency.

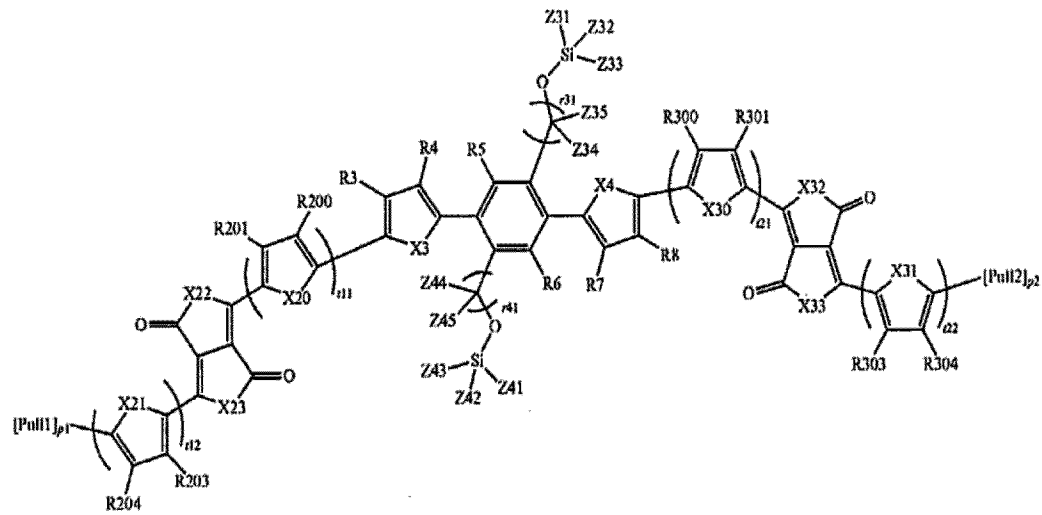

The invention claimed is:

1. A compound of Chemical Formula 1:

wherein:

n1 is an integer of 1 to 3;

m1 and m2 are each an integer of 0 to 3;

p1 and p2 are each an integer of 1 to 3 when n1, m1, m2, p1 and p2 are 2 or greater, structures in the two or more square brackets are the same as or different from each other;

Push is any one of the following structures:

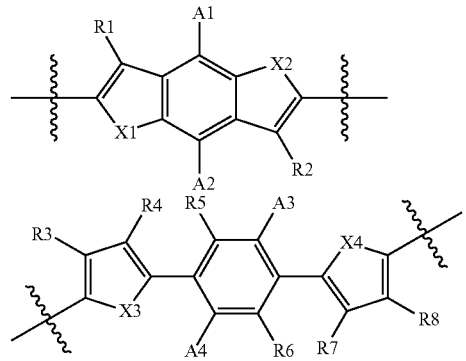

wherein:

X1 to X4 are the same as or different from each other, and each independently CRR', NR, O, SiRR', PR, S, GeRR', Se or Te;

R, R', R1 to R8, A3 and A4 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group, or R5 and R6 or A3 and A4 are represented by the following Chemical Formula 2;

A1 and A2 are the same as or different from each other, and each independently represented by the following Chemical Formula 2:

[Chemical Formula 2]

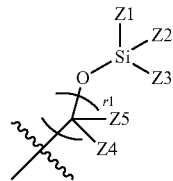

wherein:

r1 is an integer of 0 to 3;

when r1 is 2 or greater, structures in the two or more parentheses are the same as or different from each other;

Z1 to Z5 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group;

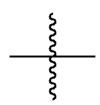

is a site bonding to Chemical Formula 1;

Linker1 and Linker2 are the same as or different from each other, and a divalent linker; and Pull1 and Pull2 are the same as or different from each other, and each independently any one of the following structures:

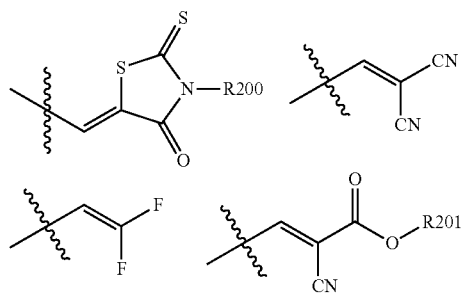

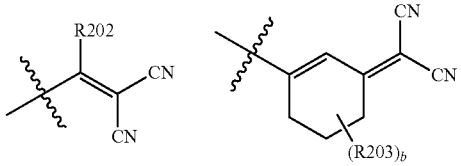

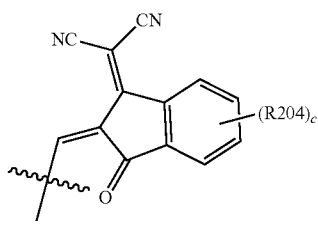

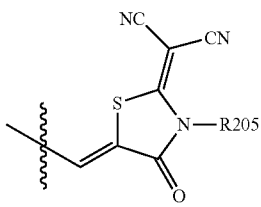

wherein:

b is an integer of 1 to 7;

c is an integer of 1 to 4;

when b and c are each 2 or greater, structures in the two or more parentheses are the same as or different from each other;

R200 to R205 are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group; and

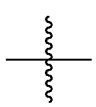

is a site bonding to Chemical Formula 1.

2. The compound of claim 1, wherein Pull1 and Pull2 have a reduction property in the compound.

3. The compound of claim 1, wherein Linker1 and Linker2 are the same as or different from each other, and each independently any one of the following structures:

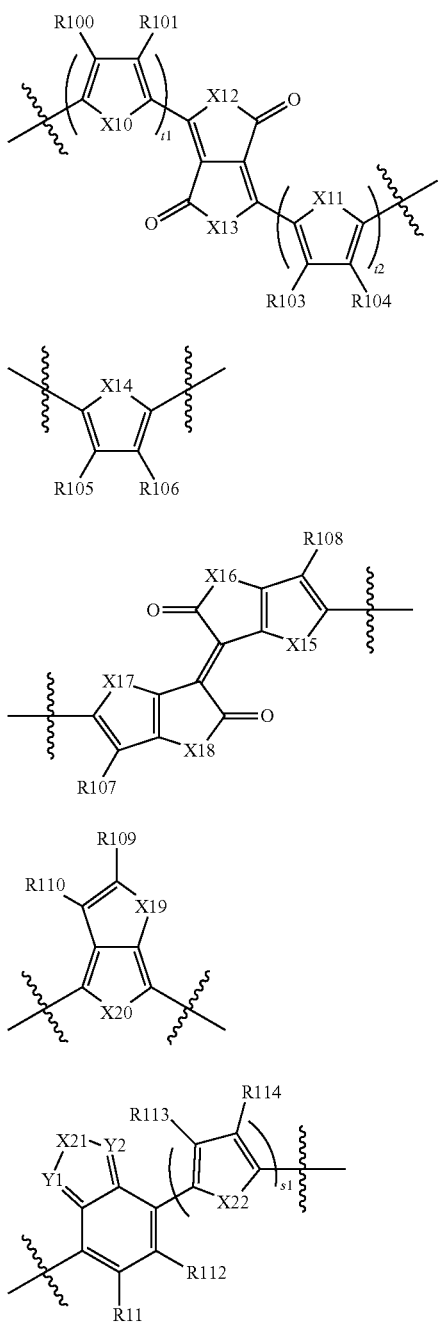

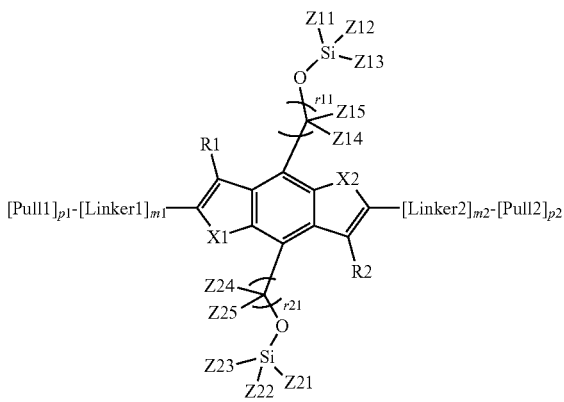

alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group; and is a site bonding to Chemical Formula 1.

4. The compound of claim 1, wherein Chemical Formula 1 is represented by any one of the following Chemical Formulae 1-2 and 1-3:

[Pull1]$_{p3}$-[Push]$_{n3}$-[Pull2]$_{p4}$ [Chemical Formula 1-2]

[Pull1]$_{p5}$-[Linker1]$_{m5}$-[Push]$_{n4}$-[Linker2]$_{m6}$-[Pull2]$_{p6}$ [Chemical Formula 1-3]

in Chemical Formulae 1-2 and 1-3, n3, n4, m5, m6 and p3 to p6 are each an integer of 1 to 3;

when n3, n4, m5, m6 and p3 to p6 are each 2 or greater, structures in the two or more square brackets are the same as or different from each other;

Push, Linker1, Linker2, Pull1 and Pull2 have the same definitions as in Chemical Formula 1; and hydrogen bonds at the end of Linker1 and Linker2.

5. The compound of claim 1, wherein the compound of Chemical Formula 1 is a compound of any one of the following Chemical Formulae 1-4 to 1-6:

[Chemical Formula 1-4]

wherein:

t1, t2 and s1 are each an integer of 1 to 3;

when t1, t2 and s1 are each 2 or greater, structures in the two or more parentheses are the same as or different from each other;

X10 to X22 are the same as or different from each other, and each independently $CR_aR_b$, $NR_a$, O, $SiR_aR_b$, $PR_a$, S, $GeR_aR_b$, Se or Te;

Y1 and Y2 are the same as or different from each other, and each independently CR", N, SiR", P or GeR";

$R_a$, $R_b$, R" and R100, R101 and R103 to R114 are the same as or different from each other, and each independently hydrogen, deuterium, a halogen group, a nitrile group, a nitro group, an imide group, an amide group, a hydroxyl group, a substituted or unsubstituted

[Chemical Formula 1-5]

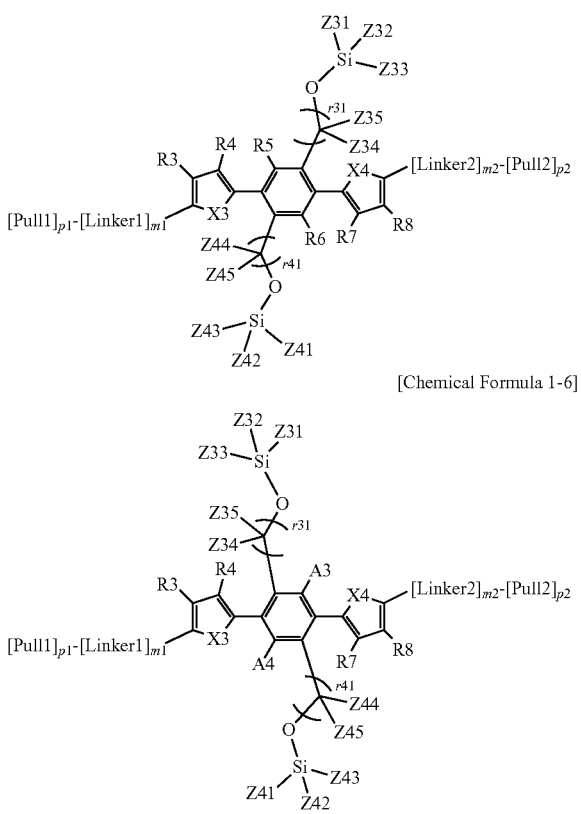

[Chemical Formula 1-6]

wherein:
m1, m2, p1, p2, Linker1, Linker2, Pull1 and Pull2 have the same definitions as in Chemical Formula 1;
X1 to X4 are the same as or different from each other, and each independently CRR', NR, O, SiRR', PR, S, GeRR', Se or Te;
R, R', R1 to R8, A3 and A4 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group;
r11, r21, r31 and r41 are each an integer of 0 to 3;
when r11, r21, r31 and r41 are 2 or greater, structures in the two or more parentheses are the same as or different from each other; and
Z11 to Z15, Z21 to Z25, Z31 to Z35 and Z41 to Z45 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group.

6. An organic solar cell comprising:
a first electrode;
a second electrode provided opposite to the first electrode; and
one or more organic material layers provided between the first electrode and the second electrode and comprising a photoactive layer,
wherein one or more layers of the organic material layers comprise the compound of claim 1.

7. The organic solar cell of claim 6, wherein the organic material layer comprises a hole transfer layer, a hole injection layer or a layer carrying out hole transfer and hole injection at the same time, and the hole transfer layer, the hole injection layer or the layer carrying out hole transfer and hole injection at the same time comprises the compound.

8. The organic solar cell of claim 6, wherein the organic material layer comprises an electron injection layer, an electron transfer layer or a layer carrying out electron injection and electron transfer at the same time, and the electron injection layer, the electron transfer layer or the layer carrying out electron injection and electron transfer at the same time comprises the compound.

9. The organic solar cell of claim 6, wherein the photoactive layer comprises one, two or more selected from the group consisting of an electron donor and an electron acceptor, and the electron donor comprises the compound.

10. The organic solar cell of claim 9, wherein the electron donor and the electron acceptor form a bulk heterojunction (BHJ).

11. The organic solar cell of claim 6, wherein the photoactive layer has a bilayer structure comprising an n-type organic material layer and a p-type organic material layer, and the p-type organic material layer comprises the compound.

12. The compound of claim 1, wherein Push is the structure:

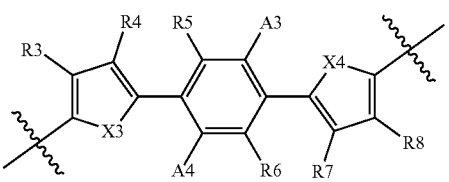

wherein R3 to R8, X3, X4, A3, A4 have the same definitions as in Chemical Formula 1.

13. The compound of claim 1, wherein Linker1 and Linker2 are the same as or different from each other, and each independently:

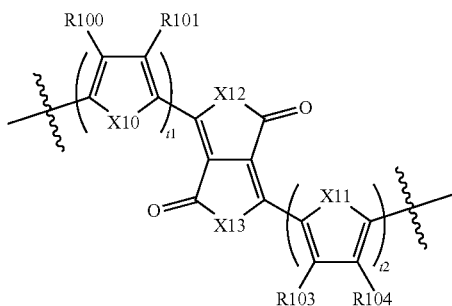

is a site bonding to Chemical Formula 1.

14. The compound of claim 1, wherein the compound is a compound of Chemical Formula 1-11:

[Chemical Formula 1-11]

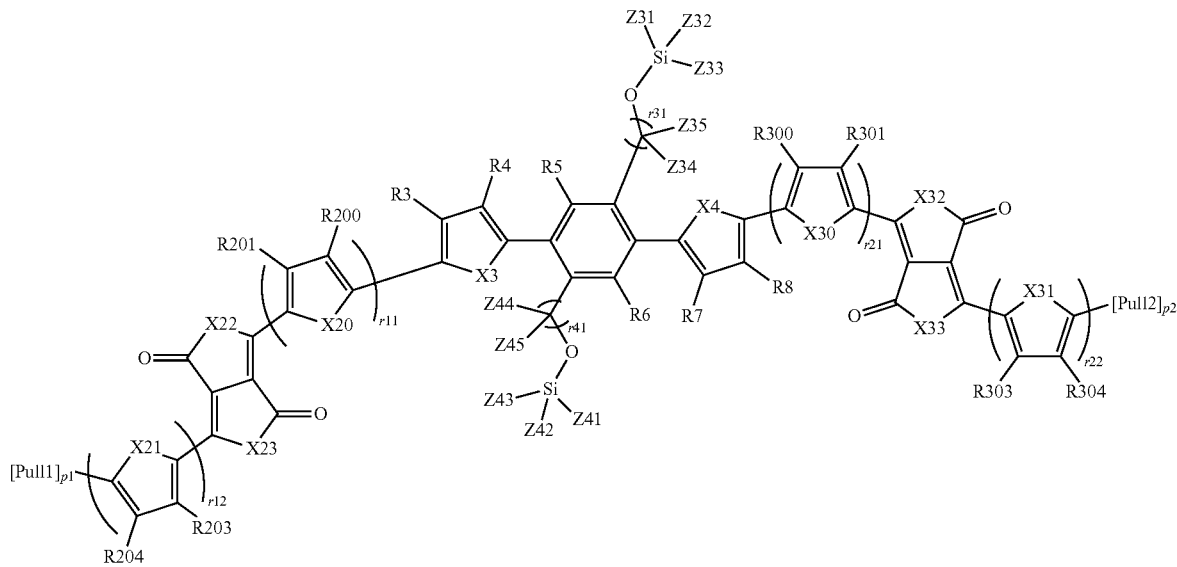

wherein:

t1 and t2 are each an integer of 1 to 3;

when t1 and t2 are each 2 or greater, structures in the two or more parentheses are the same as or different from each other;

X10 to X13 are the same as or different from each other, and each independently $CR_aR_b$, $NR_a$, O, $SiR_aR_b$, $PR_a$, S, $GeR_aR_b$, Se or Te;

$R_a$, $R_b$, and R100, R101, R103 and R104 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group; and wherein:

p1, p2, Pull1 and Pull2 have the same definitions as in Chemical Formula 1;

X3 and X4 are the same as or different from each other, and each independently CRR', NR, O, SiRR', PR, S, GeRR', Se or Te;

R, R', and R3 to R8 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group;

r31 and r41 are each an integer of 0 to 3;

when r31 and r41 are 2 or greater, structures in the two or more parentheses are the same as or different from each other;

Z31 to Z35 and Z41 to Z45 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group;

t11, t12, t21 and t22 are each an integer of 1 to 3;

when t11, t12, t21 and t22 are each 2 or greater, structures in the two or more parentheses are the same as or different from each other;

X20 to X23 and X30 to X33 are the same as or different from each other, and each independently $CR_aR_b$, $NR_a$, O, $SiR_aR_b$, $PR_a$, S, $GeR_aR_b$, Se or Te; and $R_a$, $R_b$, R200, R201, R203, R204, R300, R301, R303 and R304 are the same as or different from each other, and each independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted aryl group, or a substituted or unsubstituted heterocyclic group.

15. The compound of claim 14, wherein X3 and X4 are each S.

* * * * *

UNITED STATES PATENT AND TRADEMARK OFFICE
CERTIFICATE OF CORRECTION

PATENT NO. : 10,439,153 B2
APPLICATION NO. : 15/559377
DATED : October 8, 2019
INVENTOR(S) : Lim et al.

Page 1 of 2

It is certified that error appears in the above-identified patent and that said Letters Patent is hereby corrected as shown below:

In the Claims

Column 53, Line 50, Claim 3:
Please delete this formula:

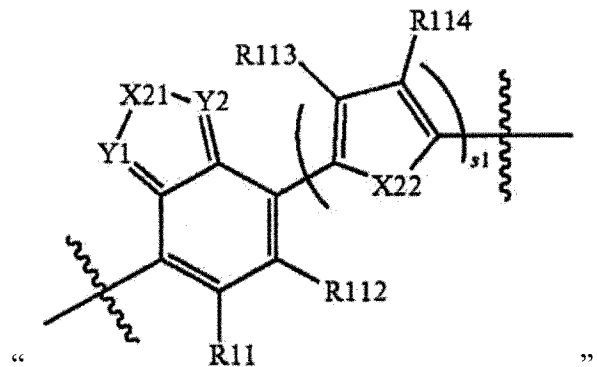

"                                      "

And replace with the following:

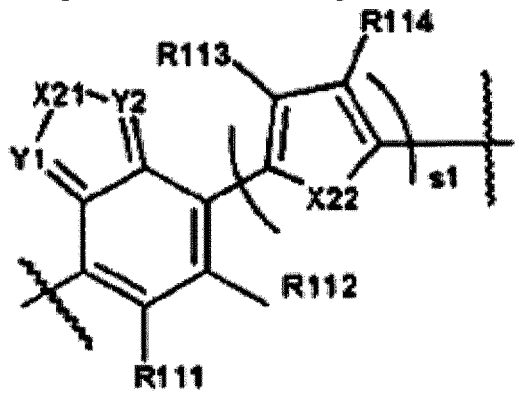

Columns 57-58, Claim 14, Chemical Formula 1-11:

Signed and Sealed this
Twenty-first Day of January, 2020

Andrei Iancu
*Director of the United States Patent and Trademark Office*

CERTIFICATE OF CORRECTION (continued)

Please delete formula 1-11 and replace with the corrected formula below: